(12) United States Patent
Otsubo et al.

(10) Patent No.: US 6,911,106 B2
(45) Date of Patent: *Jun. 28, 2005

(54) PROCESS FOR PLACEMENT OF INDICATOR ELEMENTS

(75) Inventors: Toshifumi Otsubo, Kanagawa-ken (JP); Hiroki Yamamoto, Kanagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 67 days.

This patent is subject to a terminal disclaimer.

(21) Appl. No.: 10/444,954

(22) Filed: May 27, 2003

(65) Prior Publication Data

US 2004/0040642 A1 Mar. 4, 2004

(30) Foreign Application Priority Data

May 30, 2002 (JP) ......................................... 2002-157698

(51) Int. Cl.[7] .......................... B32B 31/00; A61F 13/15
(52) U.S. Cl. ....................... 156/229; 156/161; 156/163; 156/259; 156/270; 156/64; 156/301
(58) Field of Search ............................... 156/160–163, 156/259, 265, 270, 226, 229–302, 64, 227

(56) References Cited

U.S. PATENT DOCUMENTS

| | | | |
|---|---|---|---|
| 4,249,532 A | 2/1981 | Polansky et al. | |
| 4,909,879 A | 3/1990 | Ball | |
| 5,522,809 A | 6/1996 | Larsonneur | |
| 6,033,502 A | 3/2000 | Coenen et al. | |
| 6,482,278 B1 | 11/2002 | McCabe et al. | |
| 6,515,194 B2 | 2/2003 | Neading et al. | |
| 6,837,958 B2 * | 1/2005 | Otsubo et al. | 156/259 |
| 2001/0053898 A1 | 12/2001 | Olson et al. | |
| 2002/0016579 A1 | 2/2002 | Stenberg | |
| 2002/0021220 A1 | 2/2002 | Dreyer | |
| 2002/0129888 A1 | 9/2002 | Otsubo et al. | |
| 2002/0148557 A1 | 10/2002 | Heller et al. | |
| 2003/0112999 A1 | 6/2003 | Clavert | |
| 2003/0125682 A1 | 7/2003 | Olson et al. | |
| 2003/0234069 A1 | 12/2003 | Coenen et al. | |
| 2004/0030318 A1 | 2/2004 | Karlsson et al. | |
| 2004/0064113 A1 | 4/2004 | Erdman | |

FOREIGN PATENT DOCUMENTS

| | | |
|---|---|---|
| EP | 1078620 | 2/2001 |
| EP | 1199057 | 4/2002 |
| JP | 2001-54535 | 2/2001 |
| JP | 2001-54536 | 2/2001 |
| WO | WO 99/32384 | 7/1999 |
| WO | 99/32384 | 7/1999 |

OTHER PUBLICATIONS

Patent Abstracts of Japan, Publication No. 03090602, Published Apr. 16, 1991.
Patent Abstracts of Japan, Publication No. 07313549, Published Dec. 5, 1994.
Patent Abstracts of Japan Publication No. 03090602, Apr. 16, 1991.
Patent Abstracts of Japan Publication No. 97313549, Dec. 5, 1995.

* cited by examiner

*Primary Examiner*—Sue A. Purvis
(74) *Attorney, Agent, or Firm*—Lowe Hauptman & Berner, LLP

(57) ABSTRACT

A process for placement of indicator elements in a disposable wearing article includes a step in which indication sheets each having the pair of indicator elements are placed on an outer web, a step in which the indication sheets are joined to the outer web, a step in which the outer web is cut together with the indication sheet to obtain first and second outer webs, a step in which the first and second outer webs are separated from each other, a step in which an inner web is placed upon and joined to the first and second outer webs to obtain a composite web, a step in which liquid-absorbent panels are joined onto the inner web and a step in which the composite web and the panel are cut together to obtain individual articles.

18 Claims, 30 Drawing Sheets

PROCESS FOR PLACEMENT OF INDICATOR ELEMENTS

BACKGROUND OF THE INVENTION

This invention relates to a process for placing, on respective surfaces of front and rear waist regions of a disposable wearing article both facing away from a wearer's body, a pair of indicator elements being visually recognizable from the exterior, respectively.

Japanese Patent Application No. 2001-54536A discloses a pull on-type disposable diaper including a patterned sheet and a process for making the same. This diaper comprises a liquid-pervious inner sheet lying on the side facing the wearer's body, a liquid-impervious outer sheet lying on the side facing away from the wearer's body and a liquid-absorbent core interposed between these sheets. This diaper has a front waist region, a rear waist region, a crotch region extending between these waist regions, a waist-opening and a pair of leg-openings. The patterned sheet being visually recognizable from the exterior of the diaper is attached to an inner surface of the outer sheet.

The process for making this diaper comprises the steps of joining the patterned sheet being smaller than the outer sheet to the inner surface of the outer sheet at a predetermined location, a step of joining the core to the inner surface of the outer sheet and joining the inner sheet onto the upper surface of the core. The process for making this diaper further comprises the steps of feeding, a plurality of the patterned sheets successively onto the inner surface of the outer sheet so as to be spaced one from another by a given dimension in the longitudinal direction of the outer sheet and joining the patterned sheets to the outer sheet by means of a hot melt adhesive.

According to the process for making the diaper as disclosed in the above-cited Publication, a plurality of the patterned sheets must be individually fed and joined to the inner surface of the outer sheet in each of the front and rear waist regions. Feeding and joining of the patterned sheets inevitably doubles time and labor and require additional devices as well as additional steps. Consequently, a manufacturing cost for the diaper correspondingly increases.

SUMMARY OF THE INVENTION

It is an object of this invention to provide a process for placing indicator elements at once on surfaces of front and rear waist regions facing away from the wearer's body, respectively, of a disposable wearing article and thereby to save time and labor for formation of the indicator elements.

According to this invention, there is provided a process for placement of a pair of indicator elements in a disposable wearing article which comprises a composite web and a liquid-absorbent panel joined to the composite web and is composed of front and rear waist regions and a crotch region between the waist regions wherein the indicator elements are visually recognizable from an exterior of the article.

The process has a machine direction (MD) and a cross direction (CD) crossing the MD and comprises:

a first step in which indication sheets each having the pair of indicator elements arranged side by side in the CD are successively fed onto a continuous outer web running in the MD so that the indication sheets are spaced apart one from another in the MD;

a second step in which the indication sheets are joined to the outer web with the pair of indicator elements positioned on both sides of an imaginary line extending in the MD and bisecting the outer web along the imaginary line;

a third step in which the outer web is cut together with the indication sheets along the imaginary line to obtain a first outer web and a second outer web;

a fourth step in which the first outer web and the second outer web are separated from each other in the CD;

a fifth step in which a continuous inner web running in the MD is placed upon and joined to the first and second outer webs to obtain the composite web with the indication sheets interposed between the outer web and the inner web;

a sixth step in which the liquid-absorbent panels are successively fed onto the inner web of the composite web so that the panels are spaced apart one from another in the MD and the panels are joined to the inner web of the composite web so as to overlay the indication sheets with the inner web interposed between the panels and the indication sheets; and a seventh step in which the composite web is cut between the panels adjacent to each other.

The process according to the second aspect of this invention comprises:

a first step in which an indication sheets each having the pair of indicator elements arranged side by side in the CD are successively fed under a continuous inner web running in the MD so that the indication sheets are spaced apart one from another in the MD;

a second step in which the indication sheets are joined to the inner web with the pair of indicator elements positioned on both sides of an imaginary line extending in the MD and bisecting the inner web along the imaginary line;

a third step in which the inner web is cut together with the indication sheets along the imaginary line to obtain a first inner web and a second inner web;

a fourth step in which the first inner web and the second inner web are separated from each other in the CD;

a fifth step in which a continuous outer web running in the MD is placed under and joined to the first and second inner webs to obtain the composite web with the indication sheets interposed between the inner web and the outer web;

a sixth step in which the liquid-absorbent panels are successively fed onto the first and second inner webs of said composite web so that the panels are spaced apart one from another in the MD and the panels are joined to the first and second inner webs of the composite web so as to overlay the indication sheets with the first and second inner webs interposed between the panels and the indication sheets; and a seventh step in which the composite web is cut between the panels adjacent to each other.

This invention based on the first aspect includes the following embodiments.

The second step includes a step in which first stretchable elastic members are secured in a stretched state to an upper surface of the outer web so as so to extend continuously in the MD on both sides of the indication sheets while second stretchable elastic members are secured in a stretched state to the upper surface of the outer web so as to extend in the CD between the indication sheets adjacent to each other.

One of the fifth step and the sixth step includes a step in which composite sheets are successively fed onto the inner web so that the composite sheets are spaced apart one from another and interposed between the indication sheets adjacent to each other in the MD and a step in which the inner web is joined to the composite sheet and the sixth step includes a step in which the panels are joined to the composite sheet.

The fifth step includes a step in which the inner web comprising first and second inner webs is placed upon the first outer web and the second outer web, the first inner web is joined to the first outer web and the second inner web is joined to the second outer web; wherein one of the fifth step and the sixth step includes a step in which the composite sheets are successively fed under the first and second outer webs so that the composite sheets are spaced apart one from another in the MD and interposed between the indication sheets adjacent to each other and a step in which the first and second outer webs are joined to the composite sheet; and wherein the sixth step includes a step in which the panel is joined to the composite sheet.

The fifth step includes a step the inner web comprising first and second inner webs is placed upon the first outer web and the second outer web, the first inner web is joined to the first outer web and the second inner web is joined to the second outer web; wherein one of the fifth step and the sixth step includes a step in which the composite sheets are successively fed onto the first and second outer webs so that the composite sheets are spaced apart one from another in the MD and interposed between the indication sheets adjacent to each other and a step in which the first and second outer webs are joined to the composite sheets; and wherein the sixth step includes a step in which the panel is joined to the composite sheet.

This invention based on the second aspect includes the following embodiments.

The second step includes a step in which first stretchable elastic members are secured in a stretched state to an under surface of the inner web so as to extend continuously in the MD on both sides of the indication sheets while second stretchable elastic members are secured in a stretched state to the under surface of said inner web so as to extend in the CD between the indication sheets adjacent to each other.

One of the fifth step and the sixth step includes a step in which composite sheets are successively fed onto the first and second inner webs so that the composite sheets are spaced apart one from another and interposed between the indication sheets adjacent to each other in the MD and a step in which the first and second inner webs of the composite web are joined to the composite sheet and the sixth step includes a step in which the panel is joined to the composite sheet.

This invention based both the first aspect and the second aspect includes following embodiments.

The outer web and the inner web are formed by a breathable hydrophobic fibrous nonwoven fabric and the composite sheet is formed by a breathable liquid-impervious plastic film and a breathable hydrophobic fibrous nonwoven fabric placed upon each other.

The panel comprises a breathable hydrophobic fibrous nonwoven fabric and a liquid-absorbent core underlying the fibrous nonwoven fabric.

The indication sheet is formed by one of a breathable hydrophobic fibrous nonwoven fabric and a breathable liquid-impervious plastic film.

The indicator element comprises an illustration printed on the indication sheet.

The indication sheet has the pair of indicator elements printed thereon in a relationship of mirror image.

DETAILED DESCRIPTION OF THE PREFERRED EMBODIMENTS

Details of the process according to this invention for placing an indicator element will be more fully understood from the description given hereunder in reference with the accompanying drawings.

Figure 1:
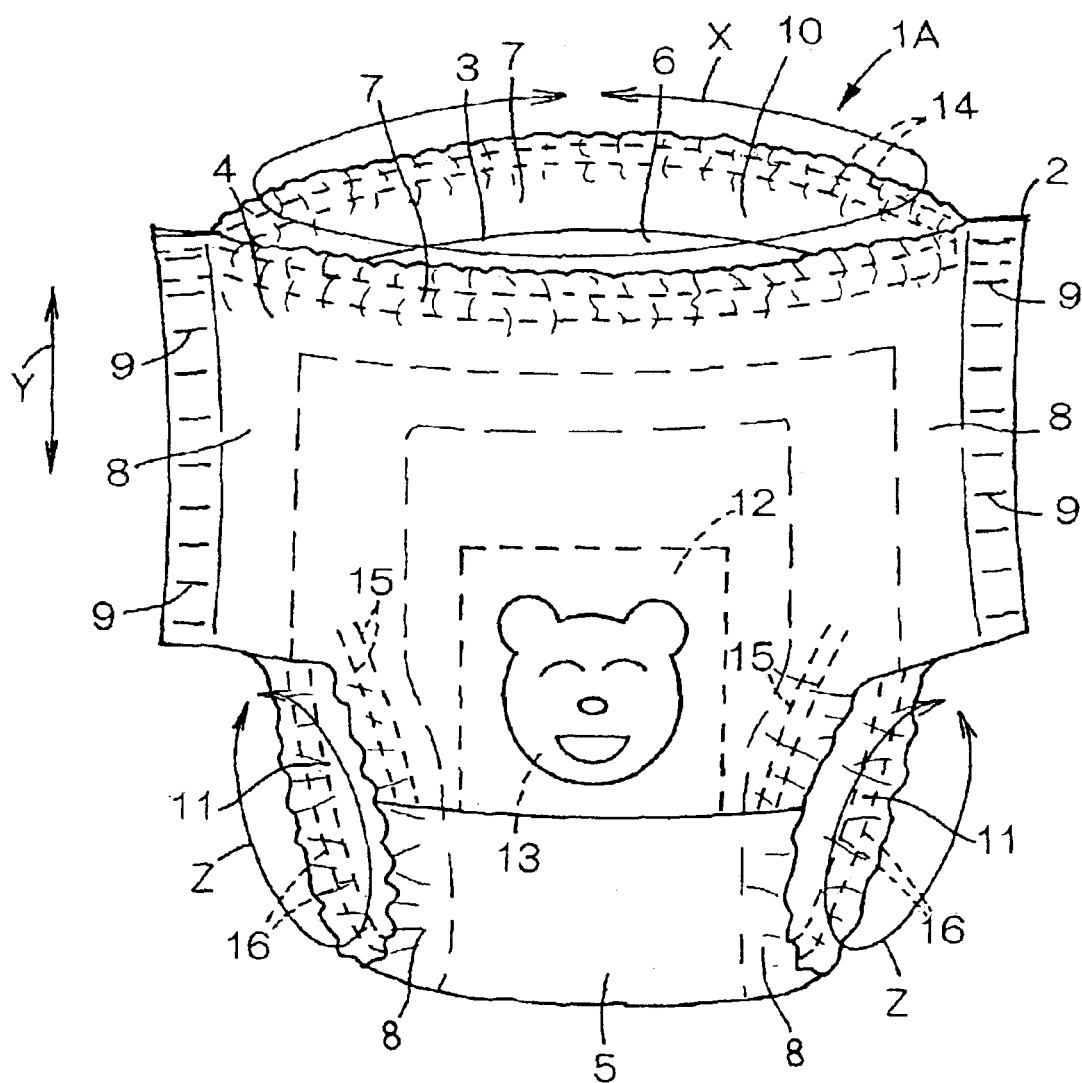
FIG. 1 is a perspective view showing an embodiment of the article adopting the process according to this invention.
Figure 2:
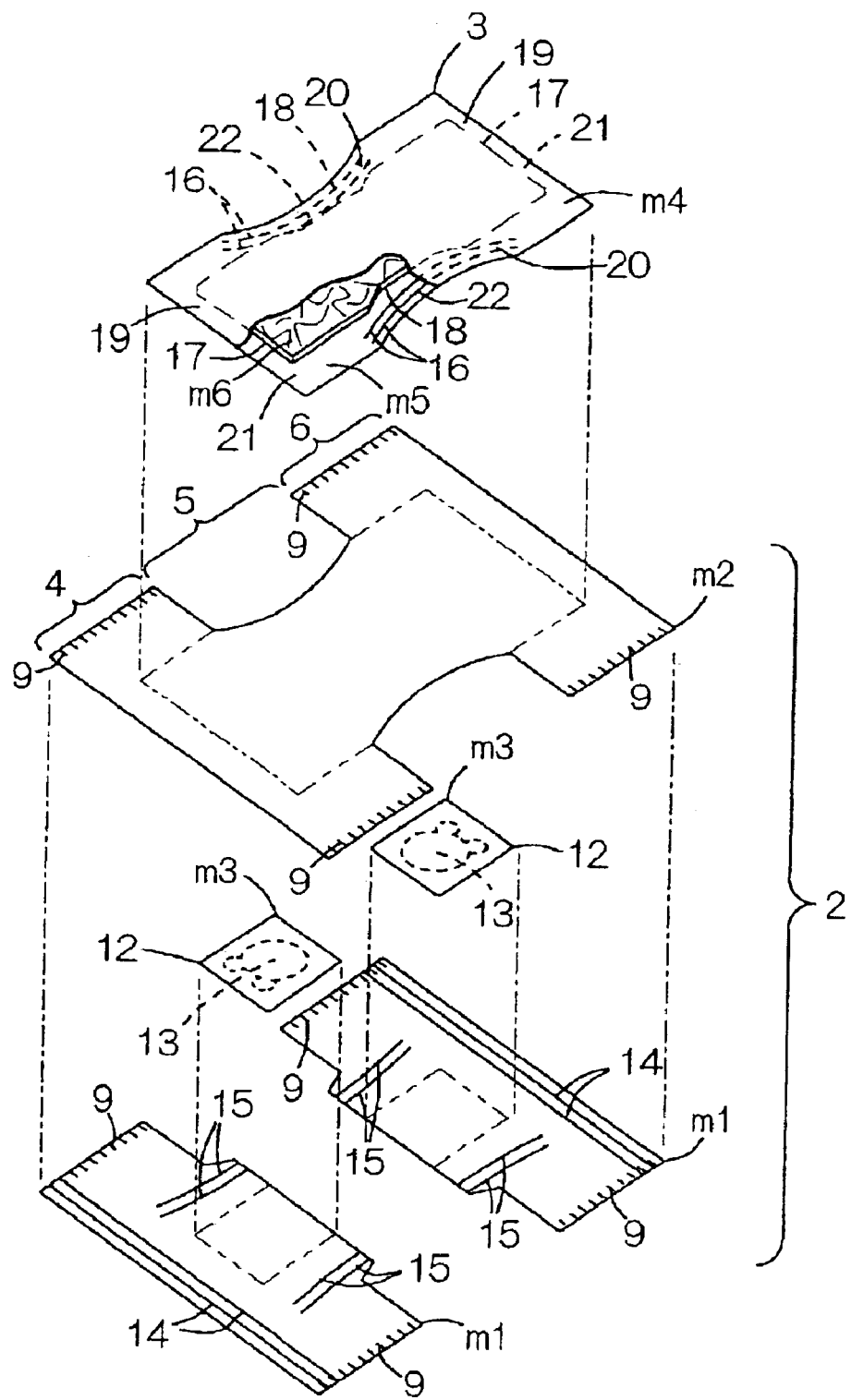
FIG. 2 is a partially cutaway exploded perspective view showing the article of FIG. 1.

FIG. 1 is a perspective view showing an embodiment 1A of the article adopting the process according to this invention for placing the indicator element and FIG. 2 is a partially cutaway perspective view showing the article 1A of FIG. 1. In FIGS. 1 and 2, a waist-circumferential direction is indicated by an arrow X, a longitudinal direction is indicated by an arrow Y and a leg-circumferential direction is indicated by an arrow Z (only in FIG. 1). Expression "inner surfaces" of first and second fibrous nonwoven fabric layers m1, m2 (outer web, inner web) constituting a composite nonwoven fabric layer 2 (composite web) and a fibrous nonwoven fabric layer m4 and a film m5 constituting a panel 3 should be understood to be surfaces facing a core m6 and expression "outer surfaces" thereof should be understood to be surfaces facing away from the core m6 (See FIG. 2).

The article 1A comprises a substantially liquid-impervious composite nonwoven fabric layer 2 (i.e., composite web) lying on the side facing away from the wearer's body and a liquid-absorbent laminated panel 3 joined to an inner surface of the composite nonwoven fabric layer 2. The article 1A is composed of front and rear waist regions 4, 6 opposed to each other and a crotch region 5 extending between these waist regions 4, 6.

The article 1A has a pair of end flaps 7 extending in a waist-circumferential direction and a pair of side flaps 8 extending in a longitudinal direction as well as in the leg-circumferential direction. In the crotch region 5, the side flaps 8 curve inward in the waist-circumferential direction of the article 1A so as to describe circular arcs. The article 1A presents a substantially hourglass-like planar shape as the article 1A is developed.

In the article 1A, the side flaps 8 are overlaid and joined together in the front and rear waist regions 4, 6 by means of a plurality of welding lines 9 arranged intermittently in the longitudinal direction. The article 1A is of pull on-type having a waist-opening 10 and a pair of leg-openings 11.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly attached to the side flaps 8.

The front and rear waist regions 4, 6 are provided in respective middle zones thereof as viewed in the waist-circumferential direction with halves of an indication sheet 12 each having an indicator element 13 adapted to be visually recognized from the exterior. The indicator element 13 comprises an illustration of a bear's face printed on the indication sheet 12. The indicator element 13 is not limited to the illustration but may be in the form of patterns, letters or figures.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web) lying on an inner surface of the nonwoven fabric layer m1. Of the composite nonwoven fabric layer 2, the first fibrous nonwoven fabric layer m1 extends in the front and rear waist regions 4, 6 while the second fibrous nonwoven fabric layer m2 extends in the front, rear and crotch regions 4, 6, 5.

The indication sheet 12 is formed by a breathable and liquid-impervious plastic film m3. It is also possible to use a breathable hydrophobic fibrous nonwoven fabric layer to form the indication sheet 12.

An inner surface of first fibrous nonwoven fabric layer m1 and an outer surface of the second fibrous nonwoven fabric layer m2 are joined together by means of a hot melt adhesive (not shown). The adhesive is applied intermittently on the first fibrous nonwoven fabric layer m1 over its whole inner surface.

The indication sheet 12 and the first and second stretchable elastic members 14, 15 are interposed between the first fibrous nonwoven fabric layer m1 and the second fibrous nonwoven fabric layer m2 and joined to the inner surface of the nonwoven fabric layer m1. The indication sheet 12 is thus not joined to the second fibrous nonwoven fabric layer m2.

In addition to the whole inner surface of the first fibrous nonwoven fabric layer m1, the outer surface of the second fibrous nonwoven fabric layer m2 also may be coated with the adhesive. In this case, the indication sheet 12 will be joined to the inner surface of the first fibrous nonwoven fabric layer m1 as well as to the outer surface of the second fibrous nonwoven fabric layer m2.

The panel 3 presents an hourglass-like planar shape and extends over the crotch region 5 into the front and rear waist regions 4, 6. The panel 3 comprises a breathable hydrophobic fibrous nonwoven fabric layer m4 lying on the side facing the wearer's body, a breathable and liquid-impervious plastic film m5 lying on the side facing away from the wearer's body and a liquid-absorbent core m6 interposed between the nonwoven fabric layer m4 and the film m5. In the panel 3, the film m5 has its outer surface joined to an inner surface of the second fibrous nonwoven fabric layer m2 by means of the hot melt adhesive (not shown).

The nonwoven fabric layer m4 is slightly larger than an upper surface of the core m6 and completely covers the upper surface of the core m6. The film m5 is slightly larger than an under surface of the core 6 and completely covers the under surface of the core m6. The nonwoven fabric layer m4 and the film m5 respectively have longitudinally opposite margins 19, 21 extending outward beyond longitudinally opposite ends 17 of the core m6 and transversely opposite lateral margins 20, 22 extending outward beyond transversely opposite side edges 18 of the core m6.

The nonwoven fabric layer m4 has its inner surface joined to the upper surface of the core m6 by means of the hot melt adhesive (not shown). The film m5 has its inner surface joined to the under surface of the core m6 by means of the hot melt adhesive (not shown). The adhesive is intermittently applied on the nonwoven fabric layer m4 over its whole inner surface as well as on the film m5 over its whole both surfaces.

The nonwoven fabric layer m4 and the film m5 are joined together along the respective longitudinally opposite margins 19, 21 and along the respective transversely opposite lateral margins 20, 22. The third stretchable elastic members 16 are interposed between the nonwoven fabric layer m4 and the film m5 and secured to the transversely opposite lateral margins 20, 22 of these nonwoven fabric layer m4 and film m5.

The core m6 comprises a mixture of fluff pulp and super-absorbent polymer particles or a mixture of fluff pulp, super-absorbent polymer particles and thermoplastic synthetic resin fibers, in any case, compressed to a desired thickness. Preferably, the core m6 is entirely wrapped with a liquid-pervious sheet such as a tissue paper or a hydrophobic fibrous nonwoven fabric layer in order to prevent the core m6 from getting out of its initial shape and/or to prevent the polymer particles from falling off from the core m6.

The end flaps 7 are defined by portions of the nonwoven fabric layers m1, m2, m4 and the film m5 extending outward beyond the longitudinally opposite ends 17 of the core m6. The side flaps 8 are defined by portions of the nonwoven fabric layers m1, m2, m4 and the film m5 extending outward in the waist-circumferential direction beyond the transversely opposite side edges 18 of the core m6.

The pattern in which the adhesive is applied on the first and second fibrous nonwoven fabric layers m1, m2, the fibrous nonwoven fabric layer m4 and the film m5 is preferably selected from the group consisting of spiral-, zigzag-, dot- and stripe-patterns. Application of the adhesive in such patterns defines the adhesive-coated zones and the adhesive-free zones in the first and second fibrous nonwoven fabric layers m1, m2, the fibrous nonwoven fabric layer m4 and the film m5.

The panel 3 may be also constituted from the breathable hydrophobic fibrous nonwoven fabric layer m4 and the liquid-absorbent core m6 joined to the inner surface of the nonwoven fabric layer m4 in the absence of the film m5. In this case, the longitudinally opposite margins 19 as well as the transversely opposite lateral margins 20 of the nonwoven fabric layer m4 and the core m6 have respectively under surfaces joined to an inner surface of the second fibrous nonwoven fabric layer m2.

Figure 3:
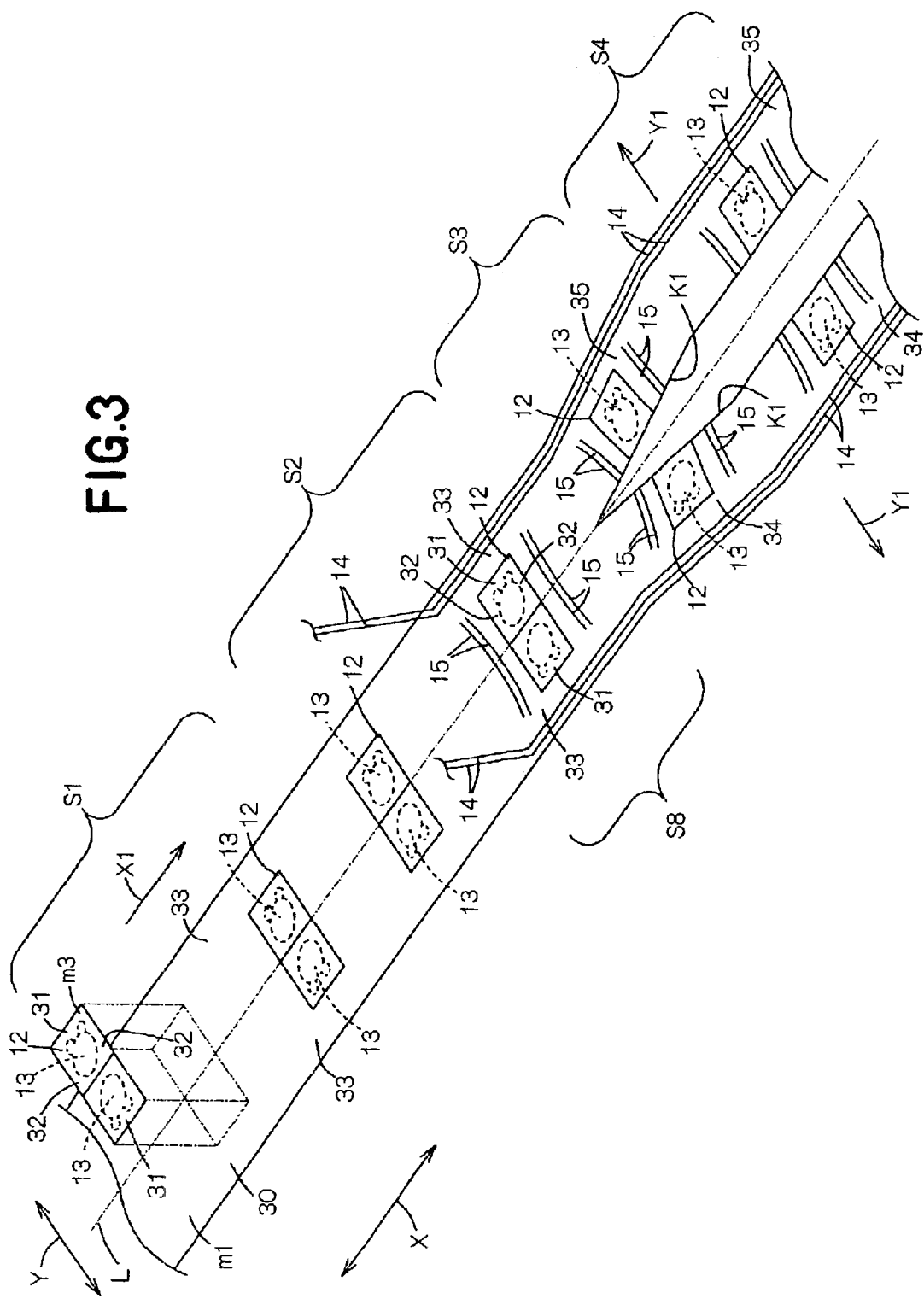
FIG. 3 is a perspective view schematically illustrating an embodiment of the process for placing an indicator element.
Figure 4:
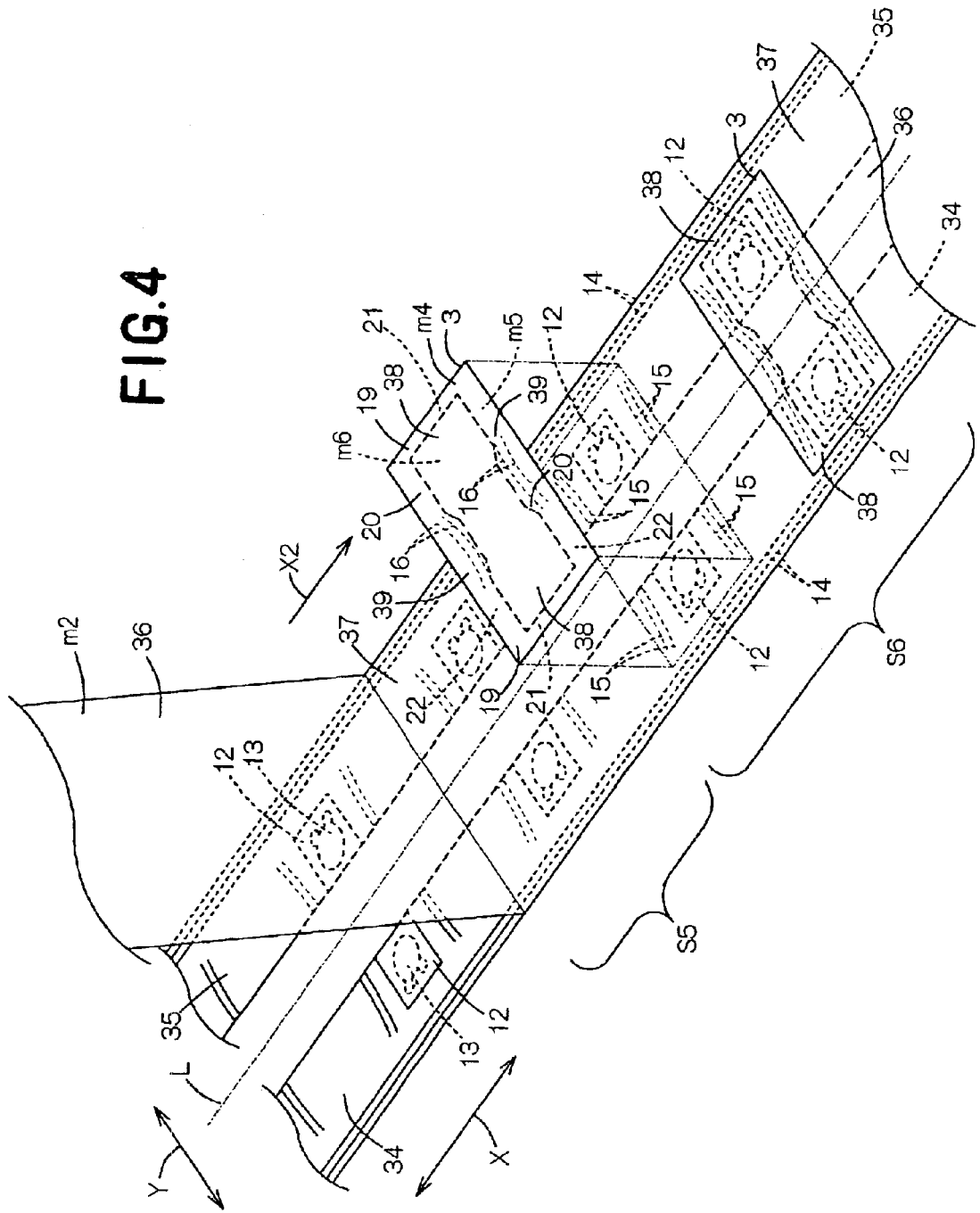
FIG. 4 is a perspective view schematically illustrating the steps subsequent to the steps in the process illustrated in FIG. 3.
Figure 5:
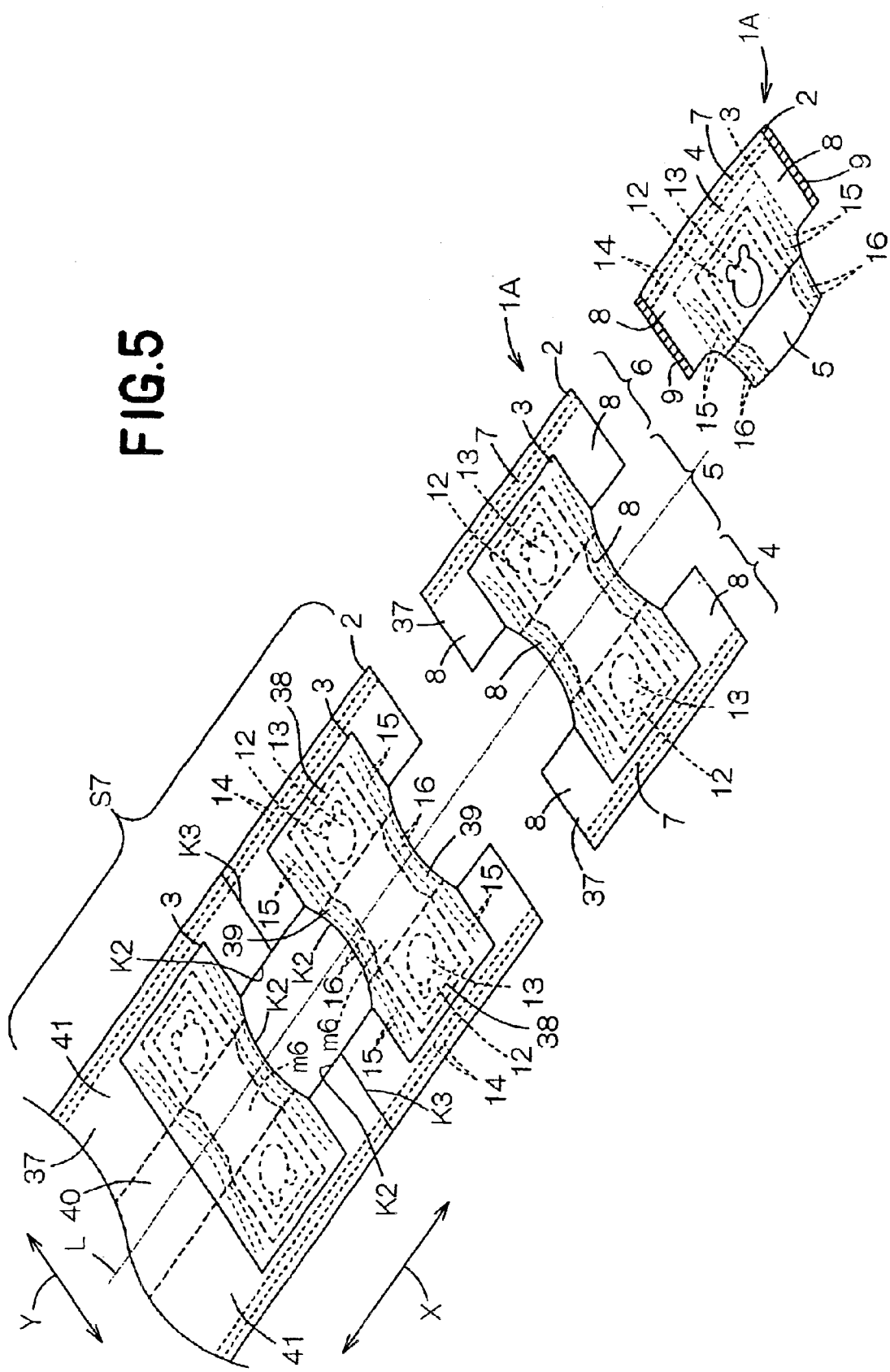
FIG. 5 is a perspective view schematically illustrating the steps subsequent to the steps in the process illustrated in FIG. 4.

FIG. 3 is a perspective view schematically illustrating an embodiment of the process for placement of the indicator elements, FIG. 4 is a perspective view schematically illustrating the steps subsequent to the steps in the process illustrated in FIG. 3 and FIG. 5 is a perspective view schematically illustrating the steps subsequent to the steps in the process illustrated in FIG. 4. Referring to these Figures, a machine direction (MD) is indicated by an arrow X and a cross direction (CD) is indicated by an arrow Y. According to this process, the article 1A of FIG. 1 is made and the indicator element 13 is formed in the front and rear waist regions 4, 6 of the article 1A through successive steps as will be described.

Step S1: In the step S1, a plurality of the indication sheets 12 each having a pair of the indicator elements 13 are successively fed onto an upper surface (i.e., inner surface) of an outer web 30 continuously running in the MD.

The outer web 30 is running at a constant speed in the MD indicated by an arrow X1. The indication sheets 12 are placed on the upper surface of the outer web 30 so as to be spaced apart one from another by a predetermined dimension in the MD.

Each of the indication sheets 12 is in form of a rectangle having long sides extending in the CD and contoured by transversely opposite ends 31 extending in the MD and longitudinal opposite side edges 32 extending in the CD. A transverse dimension of the indication sheet 12 is smaller than that of the outer web 30, so the ends 31 thereof lie inside the side edges 33 of the outer web 30. The indicator elements 13 are a pair of illustrated bear's faces arranged side by side. These illustrated bear's faces are printed on the indication sheet 12 in a mirror image relationship with each other.

The outer web 30 is formed by the breathable hydrophobic fibrous nonwoven fabric layer m1 (i.e., the first fibrous nonwoven fabric layer). The indication sheet 12 is formed by the breathable and liquid-impervious plastic film m3.

Step S2: In the step S2, the indication sheet 12 is joined to the upper surface of the outer web 30 with the individual indicator elements 13 placed on both sides of an imaginary line L extending in MD and bisecting the outer web 30. The indication sheet 12 is joined to the outer web 30 by means of the hot melt adhesive (not shown) intermittently applied on the outer web 30 over its whole upper surface.

In this step S2, a plurality of the first stretchable elastic members 14 (waist elastic members) continuously extending in the MD are secured in a stretched state to the upper surface of the outer web 30 along its transversely opposite lateral margins 33 while a plurality of the second stretchable elastic members 15 (leg elastic members) extending in the CD are secured in a stretched state to the upper surface of the outer web 30 (step S8).

The first stretchable elastic members 14 extend outside the respective lateral margins 31 of the indication sheet 12. The second stretchable elastic members 15 extend outside the transversely opposite side edges 32 of the indication sheet 12. These first and second stretchable elastic members 14, 15 are secured to the upper surface of the outer sheet 30 by means of the hot melt adhesive.

In this step S2, the outer web 30, the indication sheet 12 and the first and second stretchable elastic members 14, 15 are compressed by a pair of nip rolls (not shown) and thereby the indication sheet 12 and the first and second stretchable elastic members 14, 15 are joined to the outer web 30.

Step S3: In the step S3, the outer web 30, the indication sheet 12 and the elastic members 15 are cut along a cutting line K1 extending along the imaginary line L and bisected in the CD.

In the step S3, the outer web 30 is divided into first and second outer webs 34, 35 and at the same time each pair of indicator elements 13 are divided into the individual indicator elements 13. Of the paired indicator elements 13 printed on the indication sheet 12, the one lies on the upper surface of the first outer web 34 and the other lies on the upper surface of the second outer web 35.

Step S4: In the step S4, the first and second outer webs 34, 35 are separated from each other by a predetermined dimension in the CD indicated by an arrow Y1 with a pair of halves bisected from the indication sheet 12 being aligned with each other in the CD.

Step S5: In the step S5, an under surface (i.e., an outer surface) of an inner web 36 continuously running in the MD is placed upon the respective upper surfaces of the first and second outer webs 34, 35 and then these first and second outer webs 34, 35 are joined to the inner web 36 by means of the hot melt adhesive with the indication sheets 12 interposed therebetween.

In this step S5, the first and second outer webs 34, 35 cooperate with the inner web 36 to form a composite web 37 (i.e., the composite nonwoven fabric layer 2). The indication sheets 12 and the inner web 36 are not joined.

The inner web 36 runs forward in the MD indicated by an arrow X2 at the same speed as those outer webs 34, 35. The inner web 36 is formed by the breathable hydrophobic fibrous nonwoven fabric layer m2 (i.e., the second fibrous nonwoven fabric layer).

In the step S5, the first and second outer web 34, 35 and the inner web 36 are compressed by a pair of nip rolls (not shown) and thereby the webs 34, 35, 36 are joined to each other.

The adhesive may be applied also on the inner web 36 over its under surface in addition to the outer web 30 over its whole upper surface. In this case, the indication sheet 12 is joined to the outer web 30 as well as to the inner web 36.

Step S6: In the step S6, a plurality of the liquid-absorbent panels 3 are successively fed onto the upper surface of the inner web 36. Thus the panels 3 are placed on the upper surface of the inner web 36 so as to be spaced apart one from another in the MD by a predetermined dimension.

In the step S6, the under surface of the panel 3 is joined to the upper surface of the inner web 36 by means of the hot melt adhesive (not shown) with transversely opposite margins 38 of the panel 3 overlaying the associated indication sheet 12.

The panel 3 comprises the breathable hydrophobic fibrous nonwoven fabric layer m4, the breathable and liquid-impervious plastic film m5 and the liquid-absorbent core m6 interposed between them (See FIG. 2). The panel 3 is provided along its lateral margins 39 with the third stretchable elastic members 16 (leg elastic members) extending in the CD. These third stretchable elastic members 16 are secured in a stretched state to the panel 3.

In the panel 3, the under surface (i.e., the outer surface) of the film m5 is joined to the upper surface of the inner web 36. In the panel 3, the under surface (i.e., the inner surface) of the nonwoven fabric layer m4 is joined to the upper surface of the core m6 while the upper surface (i.e., the inner surface) of the film m5 is joined to the under surface of the core m6 by means of the hot melt adhesive (not shown). The nonwoven fabric layer m4 and the film m5 are joined together along the longitudinally opposite margins 19, 21 and the transversely opposite lateral margins 20, 22 thereof. The third stretchable elastic members 16 are joined to the nonwoven fabric layer m4 as well as to the film m5. The adhesive is intermittently applied on the nonwoven fabric layer m4 over its whole under surface as well as on the film m5 over its whole upper and under surfaces.

The panel 3 may be formed also by the breathable hydrophobic fibrous nonwoven fabric layer m4 and the liquid-absorbent core m6 joined to the inner surface of the nonwoven fabric layer m4. In this case, the longitudinally opposite margins 19 and the transversely opposite lateral margins 20 of the nonwoven fabric layer m4 and the under surface of the core m6 are joined to the upper surface of the inner web 36.

In the step S6, the composite web 37 and the panel 3 are compressed by a pair of nip rolls (not shown) and thereby joined together.

Step S7: In the step S7, the composite web 37 and the opposite lateral margins 39 of the panels 3 are cut along the lines K2, K3 between each pair of the adjacent panels 3.

In a transversely middle zone 40 of the composite web 37, each of the substantially square regions is cut out from assembly of the composite web 37 and the panels 3 along the cutting line K2 of which a pair of transverse sections are defined by the opposite lateral margins 39 of the panel 3 and thereby cutouts destined to form a periphery of the leg-opening are obtained. At the same time, in the vicinity of the transversely opposite lateral zones 41, the composite web 37 is cut along the cutting line K3 rectilinearly extending in the CD. Those regions are cut out from the assembly of the composite web 37 and the respective panels 3 are cut in this manner to obtain a plurality of the individual articles 1A.

The article 1A obtained in this manner has a substantially hourglass-like planar shape to define, as viewed in the CD of the web 37, the front waist region 4, the rear waist region 6 and the crotch region 5 extending between these waist regions 4, 6.

After the composite web 37 has been cut and the transversely opposite lateral margins 39 of the respective panels 3 have been trimmed, the composite web 37 and the associated panel 3 are folded along the imaginary line L with the panel 3 inside and the front waist region 4 and the rear waist region 6 both formed by the composite web 37 are placed upon each other. Then, these front and rear waist regions 4, 6 are joined together by means of the welding lines 9 to obtain the pull on-type article.

Figure 6:
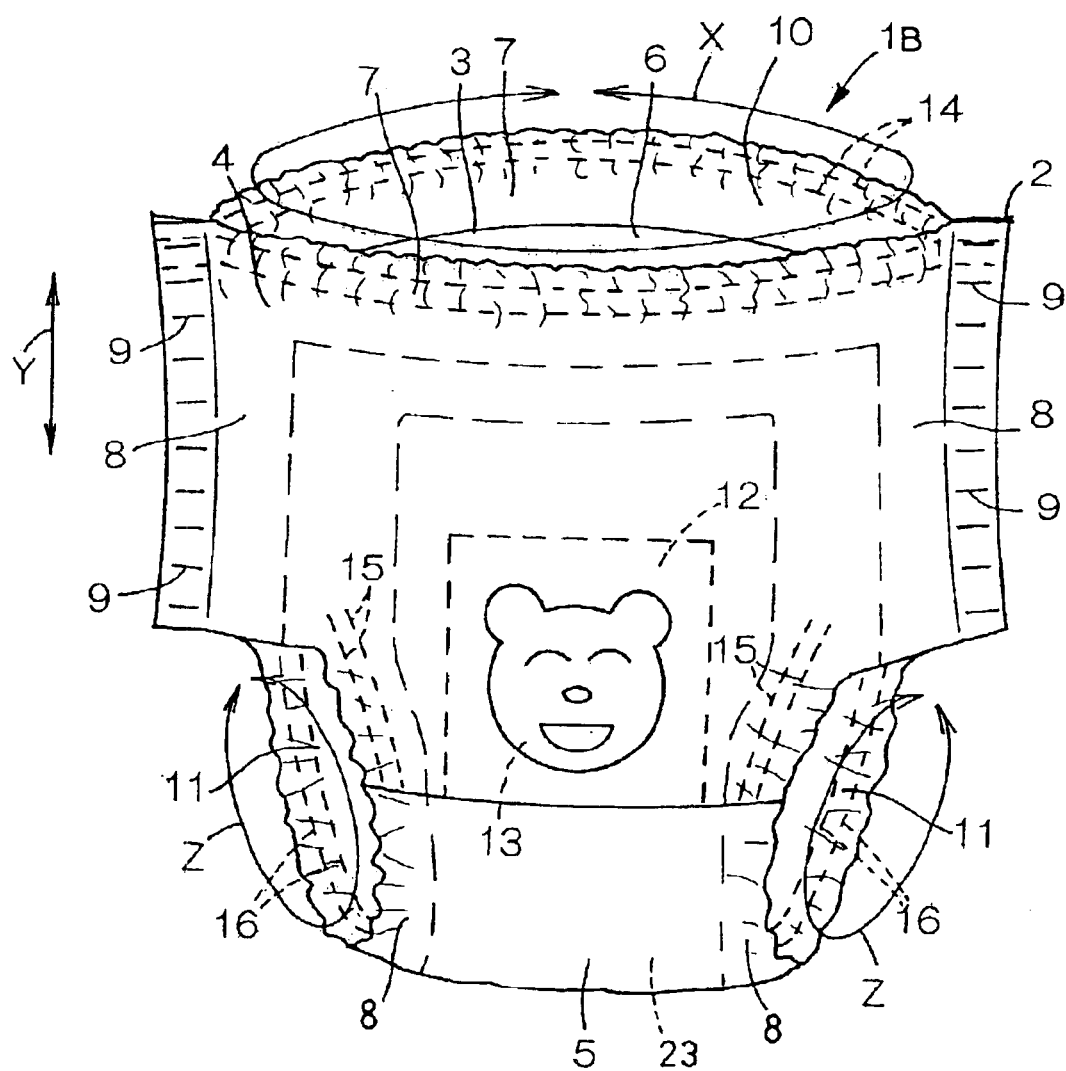
FIG. 6 is a perspective view showing another embodiment of the article adopting the process according to this invention.
Figure 7:
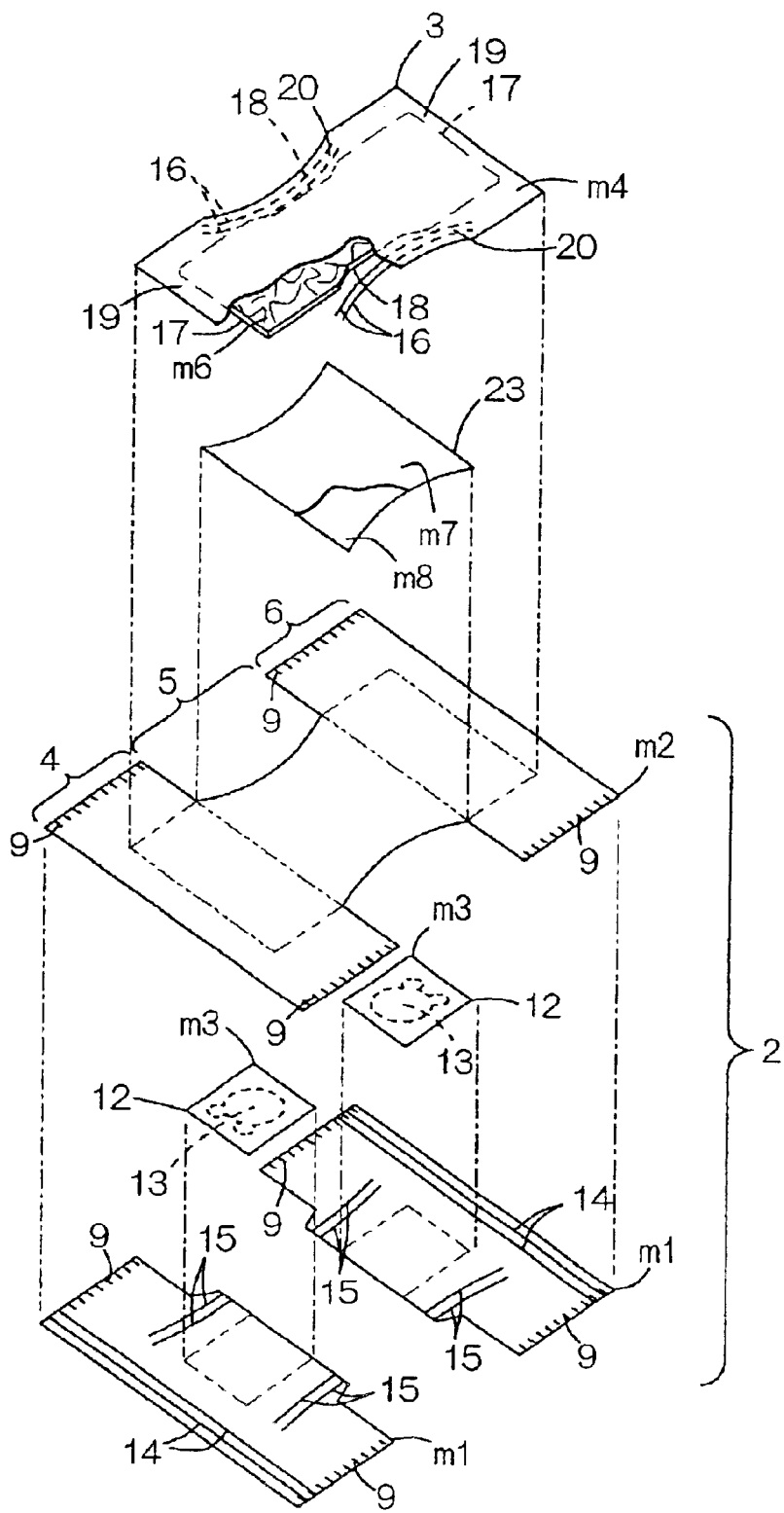
FIG. 7 is a partially cutaway perspective view showing the embodiment of the article of FIG. 6.

FIG. 6 is a perspective view showing another embodiment 1B of the article adopting the process according to this invention and FIG. 7 is a partially cutaway perspective view showing the embodiment 1B of the article of FIG. 6. In FIGS. 6 and 7, a waist-circumferential direction is indicated by an arrow X, a longitudinal direction is indicated by an arrow Y and a leg-circumferential direction is indicated by an arrow Z (only in FIG. 6). Expression "inner surfaces" of a film m7 and a nonwoven fabric layer m8 constituting a composite sheet 23 should be understood to be surfaces facing a core m6 and expression "outer surfaces" thereof should be understood to be surfaces facing away from the core m6.

The article 1B comprises a substantially liquid-impervious composite nonwoven fabric layer 2 (i.e., composite web), a liquid-impervious composite sheet 23 joined to the inner surface of the nonwoven fabric layer 2 and a liquid-absorbent panel 3 joined to the inner surfaces of the nonwoven fabric layer 2 and the sheet 23.

The article 1B is composed of front and rear waist regions 4, 6 opposed to each other, a crotch region 5 extending between these waist regions 4, 6, end flaps 7 extending in the waist-circumferential direction and side flaps 8 extending in the longitudinal direction and in the leg-circumferential direction. The article 1B is of pull on-type having a waist-opening 10 and a pair of leg-openings 11.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly secured to the side flaps 8.

The front and rear waist regions 4, 6 are provided in respective middle zones thereof as viewed in the waist-circumferential direction with the respective halves of an indication sheet 12 each having an illustration of a bear's face (indicator element 13) printed thereon. The indication sheet 12 is formed by a breathable and liquid-impervious plastic film m3.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web). An inner surface of the first fibrous nonwoven fabric layer m1 and an outer surface of the second fibrous nonwoven fabric layer m2 are joined together by means of a hot melt adhesive (not shown). The adhesive is intermittently applied on the first fibrous nonwoven fabric layer m1 over its whole inner surface.

The indication sheet 12 and the first and second stretchable elastic members 14, 15 are interposed between the first fibrous nonwoven fabric layer m1 and the second fibrous nonwoven fabric layer m2 and joined to the inner surface of the nonwoven fabric layer m1. The indication sheet 12 is thus not joined to the second fibrous nonwoven fabric layer m2.

The composite sheet 23 comprises a breathable and liquid-impervious plastic film m7 and a breathable hydrophobic fibrous nonwoven fabric layer m8 placed upon each other. The composite sheet 23 presents an hourglass-like planar shape and lies in the crotch region 5. The composite sheet 23 is smaller than the panel 3 and covers the under surface of the core m6 in the crotch region 5 (See FIG. 7). The film m7 and the nonwoven fabric layer m8 are joined together by means of the hot melt adhesive (not shown).

In the composite nonwoven fabric layer 2 and the composite sheet 23, an inner surface of the second fibrous nonwoven fabric layer m2 constituting the nonwoven fabric layer 2 is joined to an outer surface of the nonwoven fabric layer m8 constituting the sheet 23 by means of the hot melt adhesive (not shown). The composite sheet 23 overlays the indication sheet 12. The adhesive is intermittently applied on the nonwoven fabric layer m8 over its whole inner and outer surfaces.

The panel 3 comprises a breathable hydrophobic fibrous nonwoven fabric layer m4 lying on the side facing the wearer's body and the liquid-absorbent core m6 joined to an inner surface of the nonwoven fabric layer m4. The nonwoven fabric layer m4 is slightly larger than an upper surface of the core m6 and covers this upper surface over its whole area. The nonwoven fabric layer m4 has longitudinally opposite margins 19 extending outward beyond longitudinally opposite ends 17 of the core m6 and transversely opposite lateral margins 20 extending outward from transversely opposite side edges 18 of the core m6. The third stretchable elastic members 16 are secured to those lateral margins 20 of the nonwoven fabric layer m4 by means of the hot melt adhesive (not shown).

In the panel 3, the longitudinally opposite margins 19 and the transversely opposite lateral margins 20 of the nonwoven fabric layer m4 are joined to the respective inner surfaces of the second fibrous nonwoven fabric layer m2 and of the film m7 by means of the hot melt adhesive (not shown). The adhesive is intermittently applied on the nonwoven fabric layer m4 over its whole inner surface.

The end flaps 7 are defined by portions of the nonwoven fabric layers m1, m2, m4 extending outward beyond the longitudinally opposite ends 17 of the core m6. The side flaps 8 are defined by portions of the nonwoven fabric layers m1, m2, m4, m8 and the film m7 extending outward in the waist-circumferential direction beyond the transversely opposite side edges 18 of the core m6.

Figure 8:
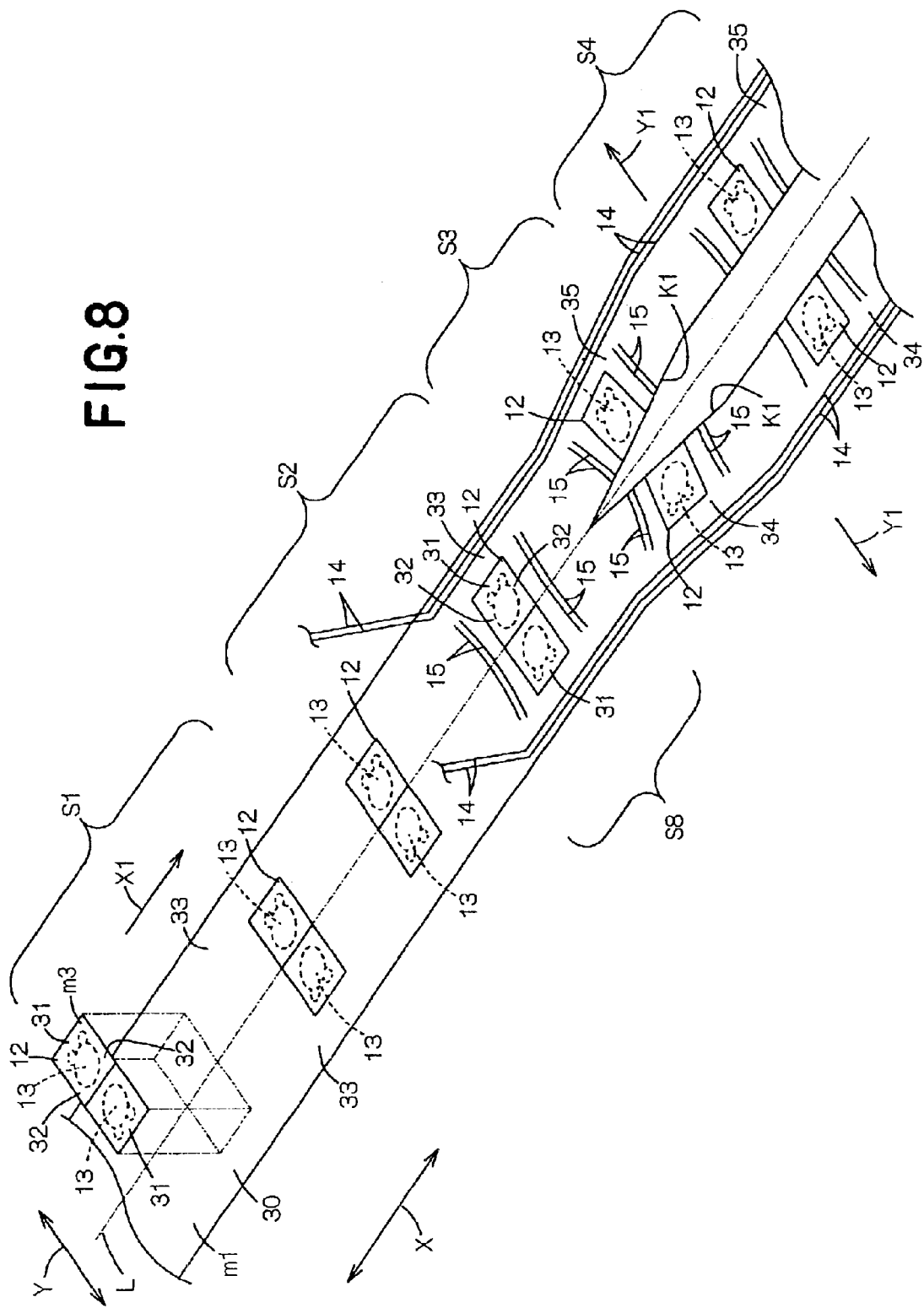
FIG. 8 is a perspective view schematically illustrating another embodiment of the process for placing the indicator element.
Figure 9:
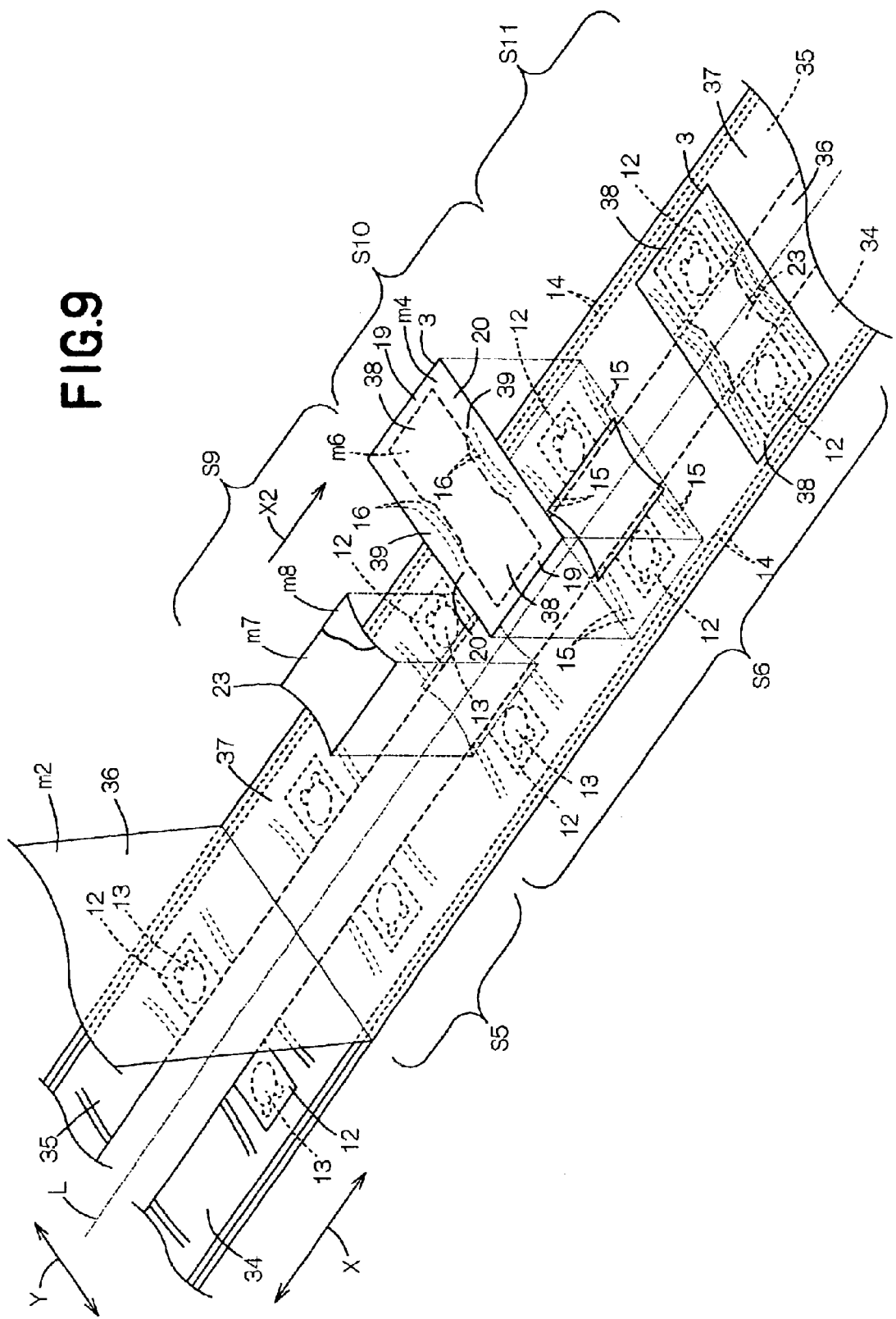
FIG. 9 is a perspective view schematically illustrating the steps subsequent to the steps in the process illustrated in FIG. 8.
Figure 10:
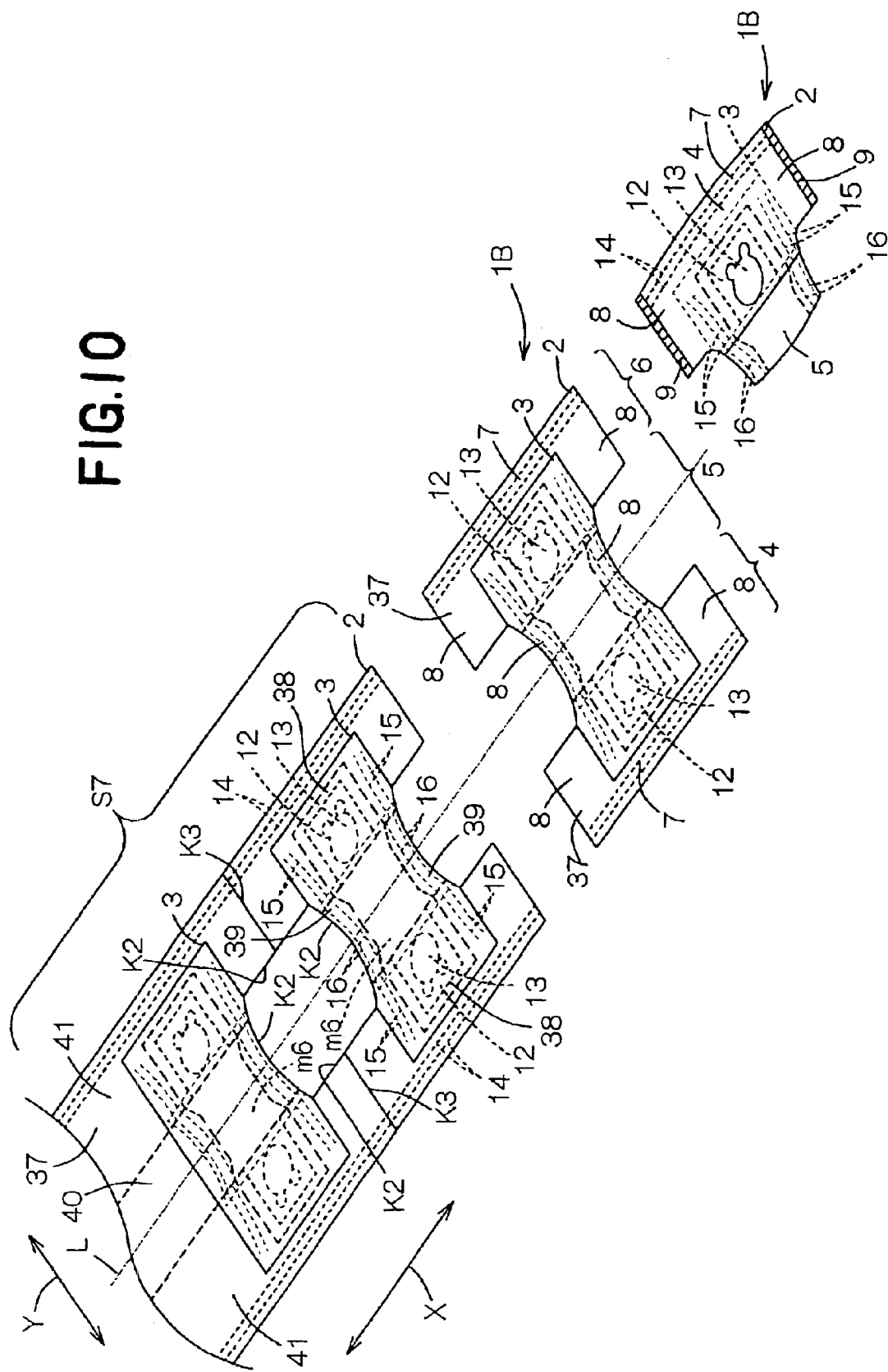
FIG. 10 is a perspective view schematically illustrating the steps subsequent to the steps in the process illustrated in FIG. 9.

FIG. 8 is a perspective view schematically illustrating another embodiment of the process for placing the indicator element, FIG. 9 is a perspective view schematically illustrating the steps subsequent to the steps in the process illustrated in FIG. 8 and FIG. 10 is a perspective view schematically illustrating the steps subsequent to the steps in the process illustrated in FIG. 9. Referring to these Figures, a machine direction (MD) is indicated by an arrow X and a cross direction (CD) is indicated by an arrow Y. According to this process, the article 1B of FIG. 6 is made and the indicator element is formed in the front and rear waist regions 4, 6 of the article 1B through successive steps as will be described.

Step S1: In the step S1, a plurality of the indication sheets 12 each having a pair of indicator elements 13 are successively fed onto an upper surface (i.e., inner surface) of an outer web 30 continuously running in the MD.

The indication sheets 12 are placed on the upper surface of the outer web 30 so as to be spaced apart one from another by a predetermined dimension in the MD. The indicator elements 13 are a pair of illustrated bear's faces arranged side by side. These illustrated bear's faces are printed on the indication sheet 12 and these two bear's faces are in mirror image relationship with each other.

The outer web 30 is formed by the breathable hydrophobic fibrous nonwoven fabric layer m1 (i.e., the first fibrous nonwoven fabric layer). The indication sheet 12 is formed by the breathable and liquid-impervious plastic film m3.

Step S2: In the step S2, the indication sheet 12 is joined to the upper surface of the outer web 30 with the individual indicator elements 13 placed on both sides of the imaginary line L. The indication sheet 12 is joined to the outer web 30 by means of the hot melt adhesive (not shown) intermittently applied on the outer web 30 over its whole upper surface.

In this step S2, a plurality of the first stretchable elastic members 14 (waist elastic members) continuously extending in the MD are secured in a stretched state to the upper surface of the outer web 30 while a plurality of the second stretchable elastic members 15 (leg elastic members) extending in the CD are secured in a stretched state to the upper surface of the outer web 30 (step S8).

Step S3: In the step S3, the outer web 30, the indication sheet 12 and the elastic members 15 are cut along a cutting line K1 extending along the imaginary line L and bisected in the CD.

In the step S3, the outer web 30 is divided into first and second outer webs 34, 35 and at the same time each pair of indicator elements 13 is divided into the individual indicator elements 13.

Step S4: In the step S4, the first and second outer webs 34, 35 are separated from each other by a predetermined dimension in the CD indicated by an arrow Y1 with a pair of halves bisected from the indication sheet 12 being aligned with each other in the CD.

Step S5: In the step S5, an under surface (i.e., an outer surface) of an inner web 36 continuously running in the MD is placed upon respective upper surfaces of the first and second outer webs 34, 35 and then these first and second outer webs 34, 35 are joined to the inner web 36.

In this step S5, the first and second outer webs 34, 35 cooperate with the inner web 36 to form a composite web 37 (i.e., the composite nonwoven fabric layer 2). The indication sheets 12 and the inner web 36 are not joined. The inner web 36 is formed by the breathable hydrophobic fibrous nonwoven fabric layer m2 (i.e., the second fibrous nonwoven fabric layer).

Step S6: In the step S6, a plurality of the composite sheets 23 are successively fed onto the upper surface (i.e., the inner surface) of the inner web 36. Thus the composite sheets 23 are placed on the upper surface of the inner web 36 so as to be spaced apart one from another in the MD (step S9).

Each of the composite sheets 23 bridges the halves of the associated indication sheet 12 having been bisected and spaced apart each other so as to overlay these halves of the indication sheet 12. The composite sheets 23 are placed on the upper surface of the inner web 36 so as to be spaced one from another in the MD by a predetermined dimension. Then the under surface of the composite sheet 23 is joined to the upper surface of the inner web 36 (step S10). The composite sheet 23 and the inner web 36 are joined together by means of the hot melt adhesive (not shown) intermittently applied on a nonwoven fabric layer m8 which will be described later more in detail over its whole under surface.

After the composite sheets 23 and the inner web 36 have been joined together, a plurality of the liquid-absorbent laminated panels 3 are successively fed onto the upper surfaces of the respective composite sheets 23. The transversely opposite margins 38 of the panel 3 lie on the associated indication sheet 12. Then, the under surface of the panel 3 is joined to the upper surface of the associated composite sheet 23 by means of the hot melt adhesive (not shown) (step S11). At the same time, the transversely opposite margins 38 of the panel 3 are joined to the upper surface of the inner web 36 by means of the hot melt adhesive (not shown).

Each of the composite sheets 23 presents an hourglass-like planar shape and comprises the breathable and liquid-impervious plastic film m7 and the breathable hydrophobic fibrous nonwoven fabric layer m8. The panel 3 comprises the breathable hydrophobic fibrous nonwoven fabric layer m4 and the liquid-absorbent core m6 underlying the nonwoven fabric layer m4 (See FIG. 7). The panel 3 is provided along its lateral margins 39 with the third stretchable elastic members 16 (leg elastic members) extending in the CD. These third stretchable elastic members 16 are secured in a stretched state to the panel 3.

In the panel 3, the under surface of the nonwoven fabric layer m4 is joined to the upper surface of the core m6 by means of the hot melt adhesive (not shown). The longitudinally opposite margins 19 and the transversely opposite lateral margins 20 of the nonwoven fabric layer m4 are joined to the upper surface of the inner web 36 as well as to an upper surface of the film m7 by means of the hot melt adhesive (not shown). The adhesive is intermittently applied on the nonwoven fabric layer m4 over its whole under surface.

The process may be implemented without departing the scope of the invention so that the composite sheets 23 are fed onto the upper surface of the inner web 36 so as to be spaced apart one from another by a predetermined dimension in the MD in the step S5 and/or the under surfaces of the respective composite sheets 23 are joined to the upper surface of the inner web 36 in the step S5.

Step S7: In the step S7, the composite web 37 and the opposite lateral margins 39 of the panels 3 are cut along the lines K2, K3 extending across the composite web 37 between each pair of the adjacent panels 3.

In a transversely middle zone 40 of the composite web 37, each of the substantially square regions is cut out from assembly of the composite web 37 and the panels 3 along the cutting line K2 of which a pair of transverse sections are defined by the opposite lateral margins 39 of the panel 3 and thereby cutouts destined to form a periphery of the leg-opening are obtained. At the same time, in the vicinity of the transversely opposite lateral zones 41, the composite web 37 is cut along the cutting line K3 rectilinearly extending in the CD. Those regions are cut out from the assembly of the composite web 37 and the respective panels 3 are cut in this manner to obtain a plurality of the individual articles 1B arranged in the MD.

The article 1B obtained in this manner has a substantially hourglass-like planar shape to define, as viewed in the CD of the web 37, the front waist region 4, the rear waist region 6 and the crotch region 5 extending between these waist regions 4, 6.

After the composite web 37 has been cut and the transversely opposite lateral margins 39 of the respective panels 3 have been trimmed, the composite web 37 and the associated panel 3 are folded along the imaginary line L with the panel 3 inside and the front waist region 4 and the rear waist region 6 both formed by the composite web 37 are placed upon each other. Then, these front and rear waist regions 4, 6 are joined together by means of the welding lines 9 to obtain the pull on-type article.

Figure 11:
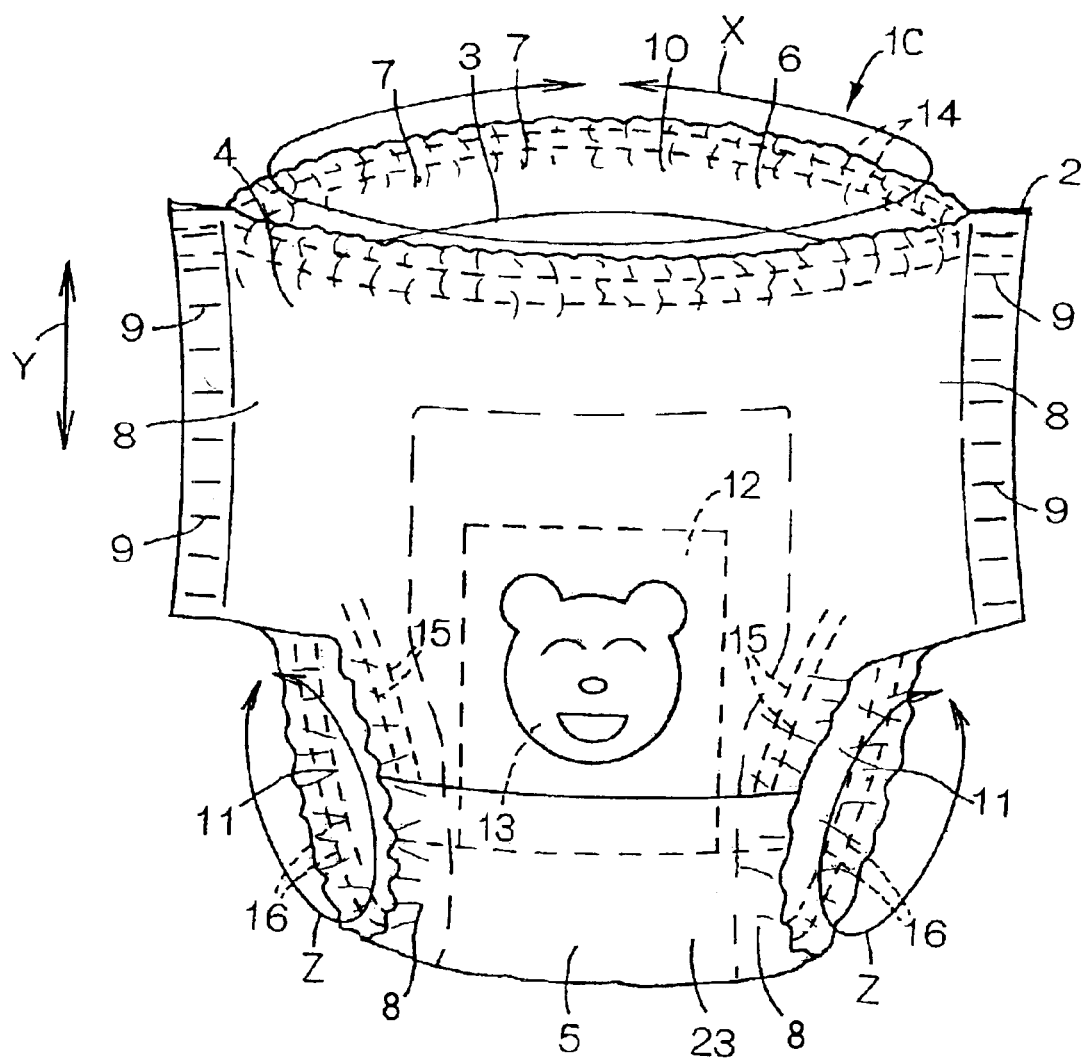
FIG. 11 is a perspective view showing still another embodiment of the article adopting the process according to this invention.
Figure 12:
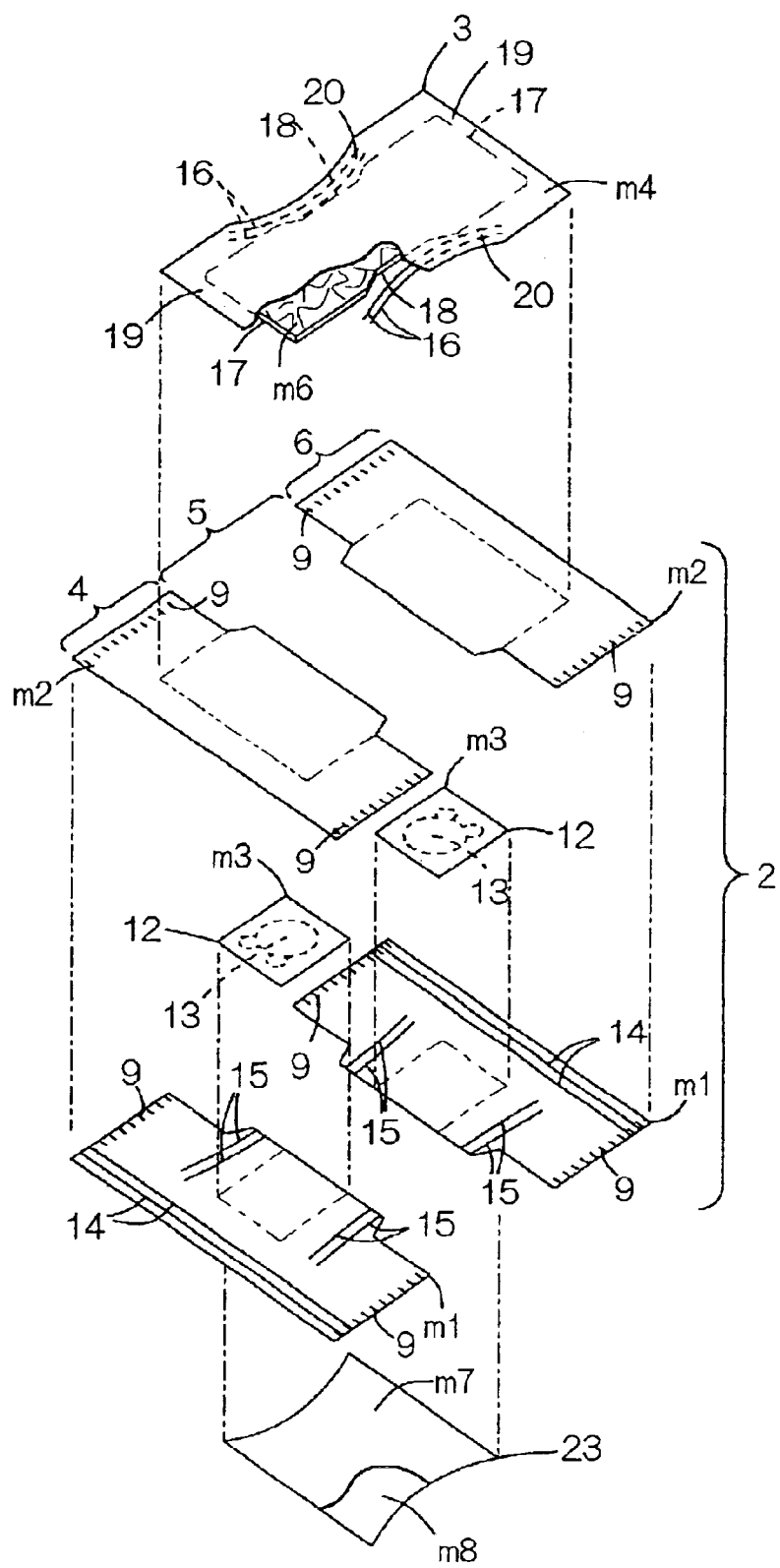
FIG. 12 is a partially cutaway perspective view showing the embodiment of the article of FIG. 11.

FIG. 11 is a perspective view showing still another embodiment 1C of the article adopting the process according to this invention and FIG. 12 is a partially cutaway perspective view showing the embodiment 1C of the article of FIG. 11. In FIGS. 11 and 12, a waist-circumferential direction is indicated by an arrow X, a longitudinal direction is indicated by an arrow Y and a leg-circumferential direction is indicated by an arrow Z (only in FIG. 11).

The article 1C comprises a substantially liquid-impervious composite nonwoven fabric layer 2 (i.e., composite web), a liquid-impervious composite sheet 23 joined to the outer surface of the nonwoven fabric layer 2 and a liquid-absorbent panel 3 joined to the inner surfaces of the nonwoven fabric layer 2 and the sheet 23, respectively.

The article 1C is composed of front and rear waist regions 4, 6 opposed to each other, a crotch region 5 extending between these waist regions 4, 6, end flaps 7 extending in the waist-circumferential direction and side flaps 8 extending in the longitudinal direction and in the leg-circumferential direction.

The article 1C is of pull on-type having a waist-opening 10 and a pair of leg-openings 11. In the article 1C, the composite nonwoven fabric layer 2 lies in the front and rear waist regions 4, 6 and the composite sheet 23 lies in the crotch region 5.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly secured to the side flaps 8.

The front and rear waist regions 4, 6 are provided in respective middle zones thereof as viewed in the waist-circumferential direction with the respective halves of an indication sheet 12 each having an illustration of a bear's face (indicator element 13) printed thereon. The indication sheet 12 is formed by a breathable and liquid-impervious plastic film m3.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web). An inner surface of the first fibrous nonwoven fabric layer m1 and an outer surface of the second fibrous nonwoven fabric layer m2 are joined together by means of a hot melt adhesive (not shown) The adhesive is intermittently applied on the first fibrous nonwoven fabric layer m1 over its whole inner surface.

The indication sheet 12 and the first and second stretchable elastic members 14, 15 are interposed between the first fibrous nonwoven fabric layer m1 and the second fibrous nonwoven fabric layer m2 and joined to an inner surface of the nonwoven fabric layer m1. The indication sheet 12 is thus not joined to the second fibrous nonwoven fabric layer m2.

The composite sheet 23 comprises a breathable and liquid-impervious plastic film m7 and a breathable hydrophobic fibrous nonwoven fabric layer m8 placed upon each other. The composite sheet 23 presents an hourglass-like planar shape and is smaller than the panel 3 and covers the under surface of the core m6 in the crotch region 5 (See FIG. 12). The composite sheet 23 overlays the indication sheet 12. The film m7 and the nonwoven fabric layer m8 are joined together by means of the hot melt adhesive (not shown).

The panel 3 comprises a breathable hydrophobic fibrous nonwoven fabric layer m4 lying on the side facing the wearer's body and the liquid-absorbent core m6 joined to an inner surface of a nonwoven fabric layer m4. The nonwoven fabric layer m4 is slightly larger than an upper surface of the core m6 and covers this upper surface over its whole area. The nonwoven fabric layer m4 has longitudinally opposite margins 19 extending outward beyond longitudinally opposite ends 17 of the core m6 and transversely opposite lateral margins 20 extending outward from transversely opposite side edges 18 of the core m6. The third stretchable elastic members 16 are secured to those lateral margins 20 of the nonwoven fabric layer m4 by means of the hot melt adhesive (not shown).

In the panel 3, the longitudinally opposite margins 19 and the transversely opposite lateral margins 20 of the nonwoven fabric layer m4 lying in the front and rear waist regions 4, 6, respectively, are joined to the inner surface of the second fibrous nonwoven fabric layer m2 by means of the hot melt adhesive (not shown) while the under surface of the core m6 and the lateral margins 20 of the nonwoven fabric layer m4 are joined to an inner surface of the film m7 by means of the hot melt adhesive (not shown). The adhesive is intermittently applied on the nonwoven fabric layer m4 over its whole inner surface and on the film m7 over its whole inner surface.

The end flaps 7 are defined by portions of the nonwoven fabric layers m1, m2, m4 extending outward beyond the longitudinally opposite ends 17 of the core m6. The side flaps 8 are defined by portions of the nonwoven fabric layers m1, m2, m4, m8 and the film m7 extending outward in the waist-circumferential direction beyond the transversely opposite side edges 18 of the core m6.

Figure 13:
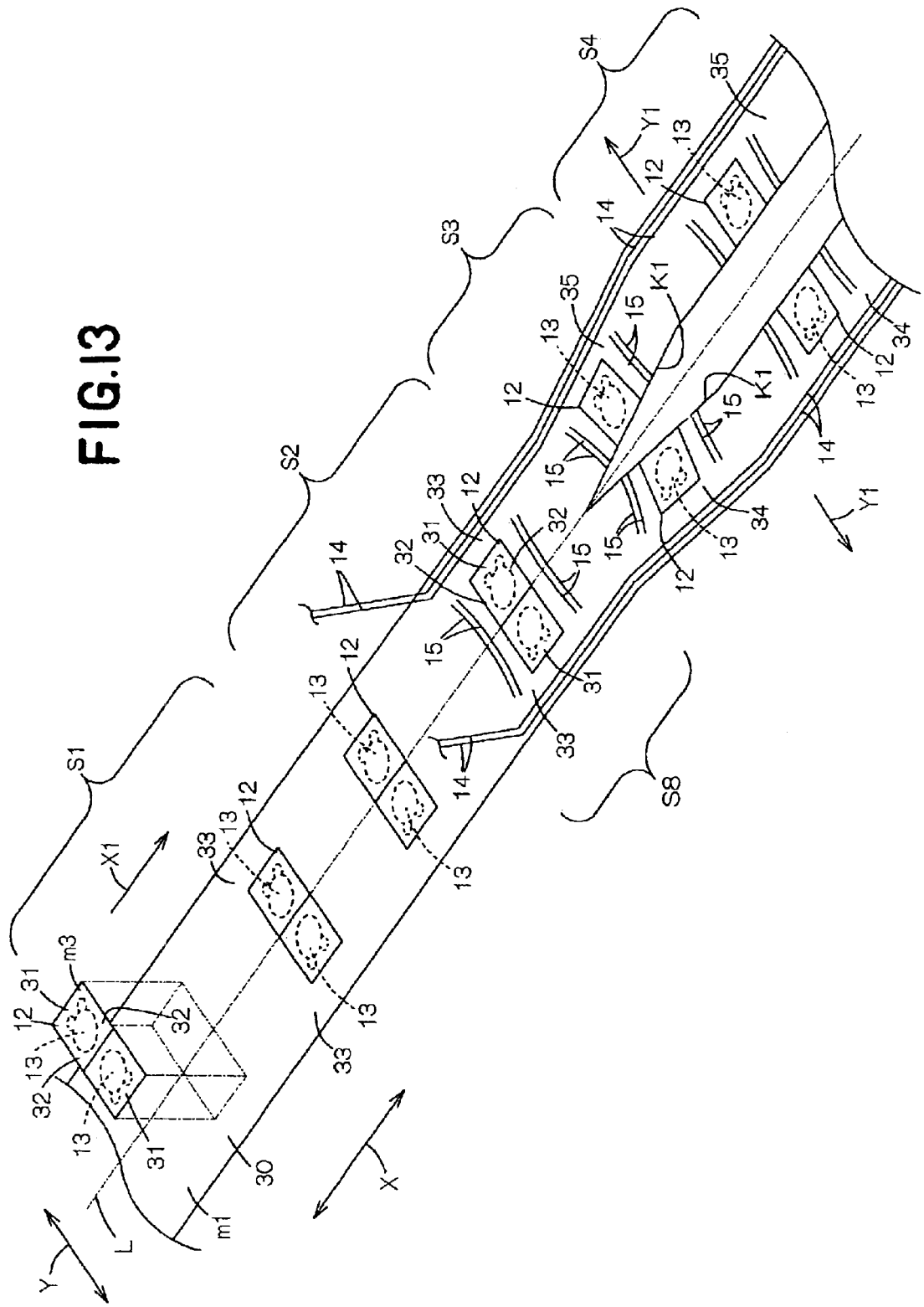
FIG. 13 is a perspective view schematically illustrating still another embodiment of the process for placing the indicator element.
Figure 14:
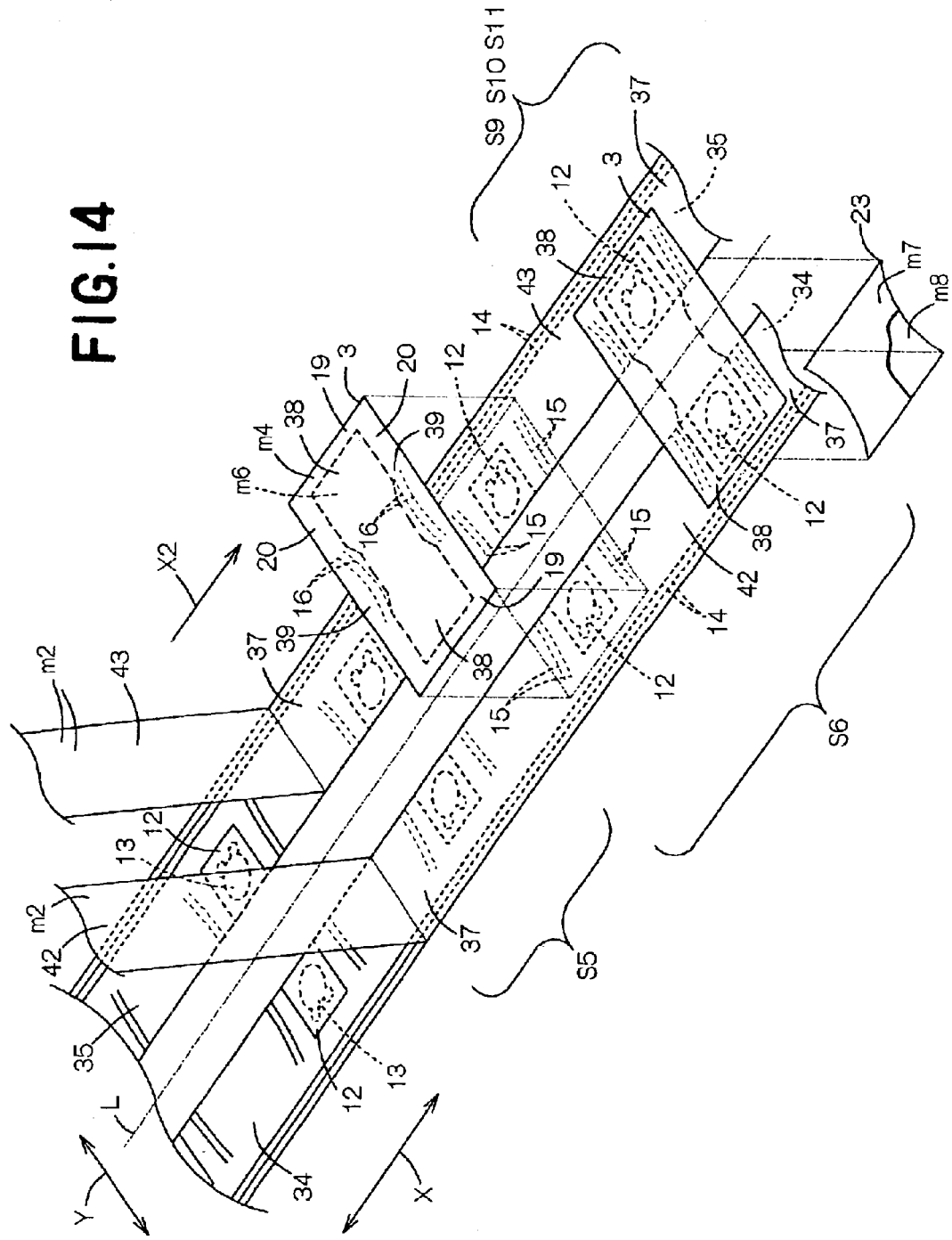
FIG. 14 is a perspective view schematically illustrating the steps subsequent to the steps in the process illustrated in FIG. 13.
Figure 15:
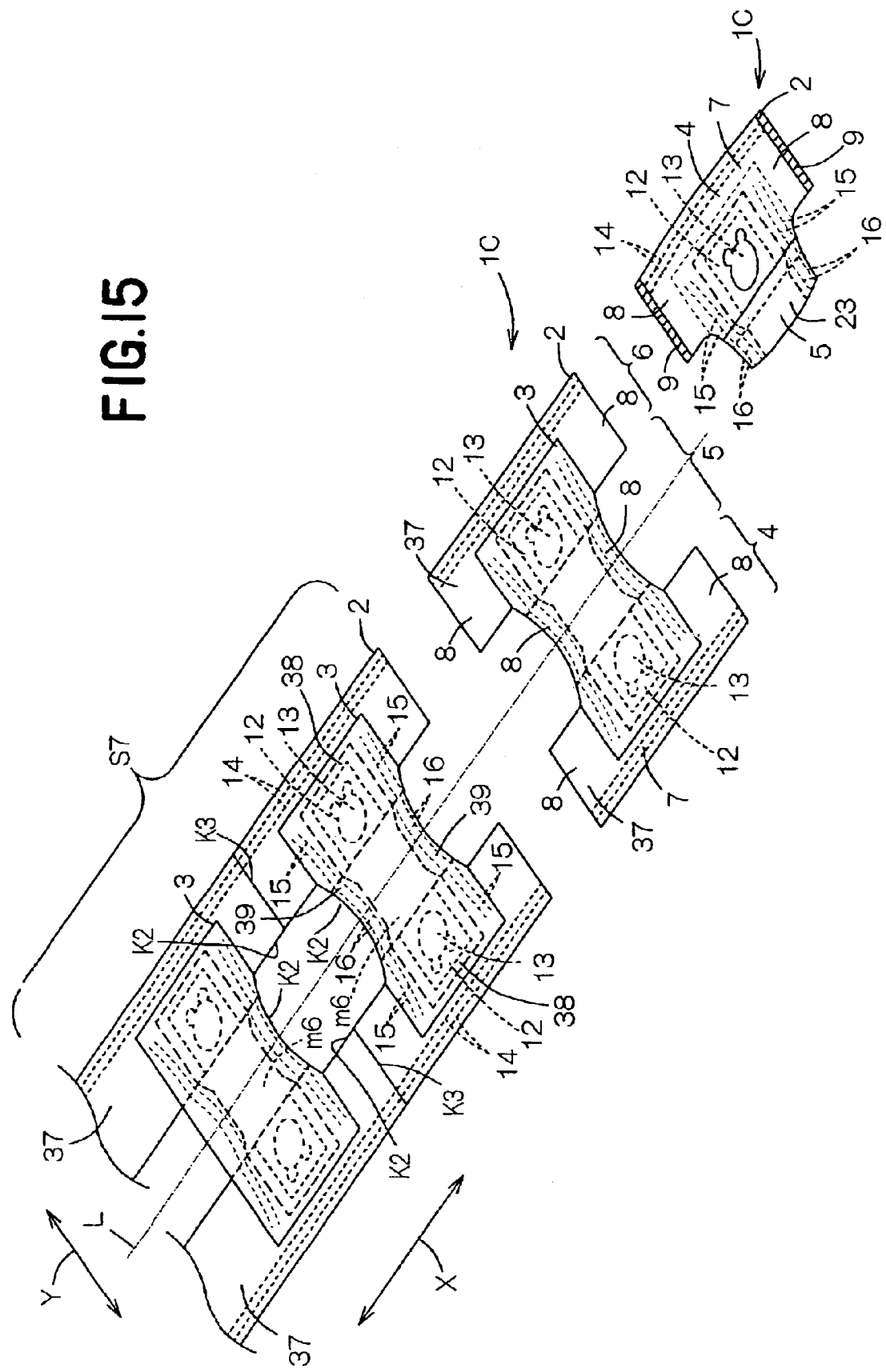
FIG. 15 is a perspective view schematically illustrating the steps subsequent to the steps in the process illustrated in FIG. 14.

FIG. 13 is a perspective view schematically illustrating still another embodiment of the process for placement of the indicator elements, FIG. 14 is a perspective view schematically illustrating the steps subsequent to the steps in the process illustrated in FIG. 13 and FIG. 15 is a perspective view schematically illustrating the steps subsequent to the steps in the process illustrated in FIG. 14. Referring to these Figures, a machine direction (MD) is indicated by an arrow X and a cross direction (CD) is indicated by an arrow Y. According to this process, the article IC of FIG. 11 is made and the indicator element is formed in the front and rear waist regions 4, 6 of the article 1C through successive steps as will be described.

Step S1: In the step S1, a plurality of the indication sheets 12 each having a pair of indicator elements 13 are successively fed onto an upper surface (i.e., inner surface) of an outer web 30 continuously running in the MD. The indication sheets 12 are placed on the upper surface of the outer web 30 so as to be spaced apart one from another by a predetermined dimension in the MD. The indicator elements 13 are a pair of illustrated bear's faces arranged side by side. These illustrated bear's faces are printed on the indication sheet 12 and these two bear's faces are in mirror image relationship with each other.

The outer web 30 is formed by the breathable hydrophobic fibrous nonwoven fabric layer m1 (i.e., the first fibrous nonwoven fabric layer). The indication sheet 12 is formed by the breathable and liquid-impervious plastic film m3.

Step S2: In the step S2, the indication sheet 12 is joined to the upper surface of the outer web 30 with the individual indicator elements 13 placed on both sides of the imaginary line L. The indication sheet 12 is joined to the outer web 30 by means of the hot melt adhesive (not shown) intermittently applied on the outer web 30 over its whole upper surface.

In this step S2, a plurality of the first stretchable elastic members 14 (waist elastic members) continuously extending in the MD are secured in a stretched state to the upper surface of the outer web 30 while a plurality of the second stretchable elastic members 15 (leg elastic members) extending in the CD are secured in a stretched state to the upper surface of the outer web 30 (step S8).

Step S3: In the step S3, the outer web 30, the indication sheet 12 and the elastic members 15 are cut along a cutting line K1 extending along the imaginary line L and bisected in the CD.

In the step S3, the outer web 30 is divided into first and second outer webs 34, 35 and at the same time each pair of the indicator elements 13 is divided into the individual indicator elements 13.

Step S4: In the step S4, the first outer web 34 and the second outer web 35 are separated from each other by a predetermined dimension in the CD indicated by an arrow Y1 with a pair of halves bisected from the indication sheet 12 being aligned with each other in the CD.

Step S5: In the step S5, under surfaces (i.e., outer surfaces) of first and second inner webs 42, 43 continuously running in the MD are placed upon upper surfaces of the first and second outer webs 34, 35, respectively and then the first outer web 34 and the first inner web 42 are joined together while the second outer web 35 and the second inner web 43 are joined together.

In this step 5, the first and second outer webs 34, 35 cooperate with the first and second inner web 42, 43 to form a composite web 37 (i.e., the composite nonwoven fabric layer 2). The indication sheets 12 and the inner webs 42, 43 are not joined. Each of the first and second inner webs 42, 43 is formed by the breathable hydrophobic fibrous nonwoven fabric layer m2 (i.e., the second fibrous nonwoven fabric layer).

Step S6: In the step S6, a plurality of the liquid-absorbent panels 3 each extending in the CD are successively fed onto upper surfaces (i.e., inner surfaces) of the first and second inner webs 42, 43. Thus the panels 3 are placed on the respective upper surfaces of the inner webs 42, 43 so as to be spaced apart one from another by a predetermined dimension in the MD.

In the step S6, the respective upper surfaces of the first and second inner webs 42, 43 are joined to the under surface of the panel 3 by means of the hot melt adhesive (not shown) with the transversely opposite margins 38 being positioned on the indication sheet 12.

Then a plurality of the composite sheets 23 are successively fed under the surfaces of the first and second outer webs 34, 35 so as to be spaced apart one from another by a predetermined dimension in the MD (step S9). Each of the composite sheets 23 bridges the halves of the associated indication sheet 12 having been bisected and spaced apart from each other so as to overlay these halves of the indication sheet 12.

In the step S6, the upper surface of the composite sheet 23 is joined to the under surfaces (i.e., the outer surfaces) of the first and second outer webs 34, 35 and to the under surface of the panel 3 by means of the hot melt adhesive (not shown) (steps S10, S11).

Each of the composite sheets 23 presents an hourglass-like planar shape and comprises the breathable and liquid-impervious plastic film m7 and the breathable hydrophobic fibrous nonwoven fabric layer m8. The panel 3 comprises the breathable hydrophobic fibrous nonwoven fabric layer m4 and the liquid-absorbent core m6 underlying the nonwoven fabric layer m4 (See FIG. 12). The panel 3 is provided along its lateral margins 39 with the stretchable elastic members 16 (leg elastic members) extending in the CD. These stretchable elastic members 16 are secured in a stretched state to the panel 3.

In the panel 3, the under surface of the nonwoven fabric layer m4 is joined to the upper surface of the core m6 by means of the hot melt adhesive (not shown). The longitudinally opposite margins 19 and the transversely opposite lateral margins 20 of the nonwoven fabric layer m4 are joined to the upper surfaces of the inner webs 42, 43 as well as to the upper surface of the film m7 by means of the hot melt adhesive (not shown). The under surface of the core m6 is joined to the upper surface of the film m7 by means of the hot melt adhesive (not shown). The adhesive is applied on the nonwoven fabric layer m4 over its whole under surface and on the film m7 over its whole upper surface.

The process may be implemented without departing the scope of the invention so that the composite sheets 23 are fed under the first and second outer webs 34, 35 so as to be spaced apart one from another by a predetermined dimension in the MD and/or the upper surface of the composite sheet 23 is joined to the under surfaces of the first and second outer webs 34, 35 in the step S5.

Step S7: In the step S7, the composite web 37 and the opposite lateral margins 39 of the panels 3 are cut along the lines K2, K3 extending across the composite web 37 between each pair of the adjacent panels 3.

Between the halves of the composite web 37 having been separated in the CD from each other, each of the substantially square regions is cut out from assembly of the composite web 37 and the opposite lateral margins 39 of the panels 3 along the cutting line K2 of which a pair of transverse sections describe circular arcs being convex toward the core m6 and thereby cutouts destined to form a periphery of the leg-opening are obtained. At the same time, the composite web 37 is cut along the cutting line K3 rectilinearly extending in the CD. Those regions are cut out from the assembly of the composite web 37 and the opposite lateral margins 39 of the panel 3 in this manner to obtain a plurality of the individual articles 1C.

The article 1C obtained in this manner has a substantially hourglass-like planar shape to define, as viewed in the CD of the web 37, the front waist region 4, the rear waist region 6 and the crotch region 5 extending between these waist regions 4, 6.

After the composite web 37 has been cut and the transversely opposite lateral margins 39 of the respective panels 3 have been trimmed, the composite web 37 and the associated panel 3 are folded along the imaginary line L with the panel 3 inside and the front waist region 4 and the rear waist region 6 both formed by the composite web 37 are placed upon each other. Then, these front and rear waist regions 4, 6 are joined together by means of the welding lines 9 to obtain the pull on-type article.

Figure 16:
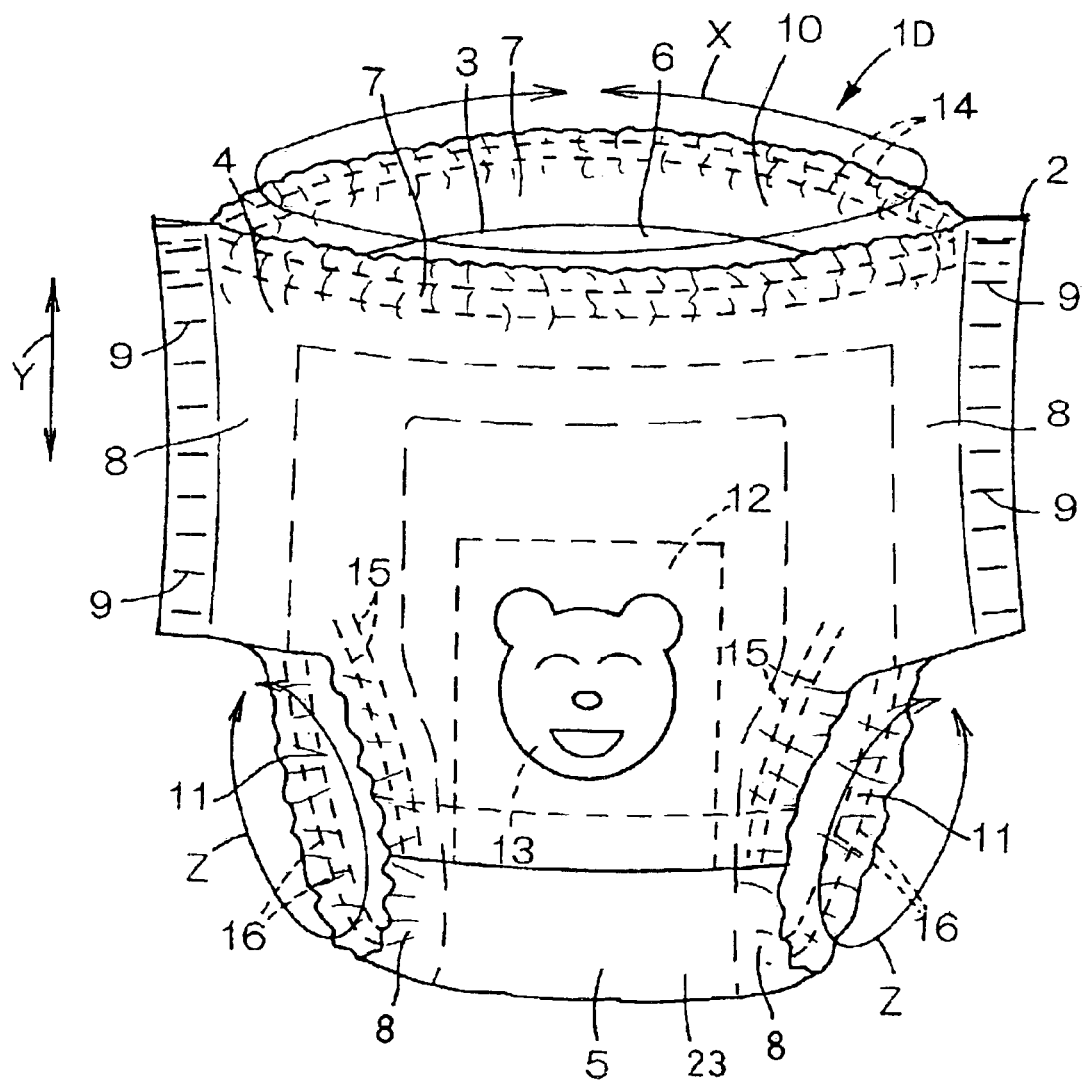
FIG. 16 is a perspective view showing further another embodiment of the article adopting the process according to this invention.
Figure 17:
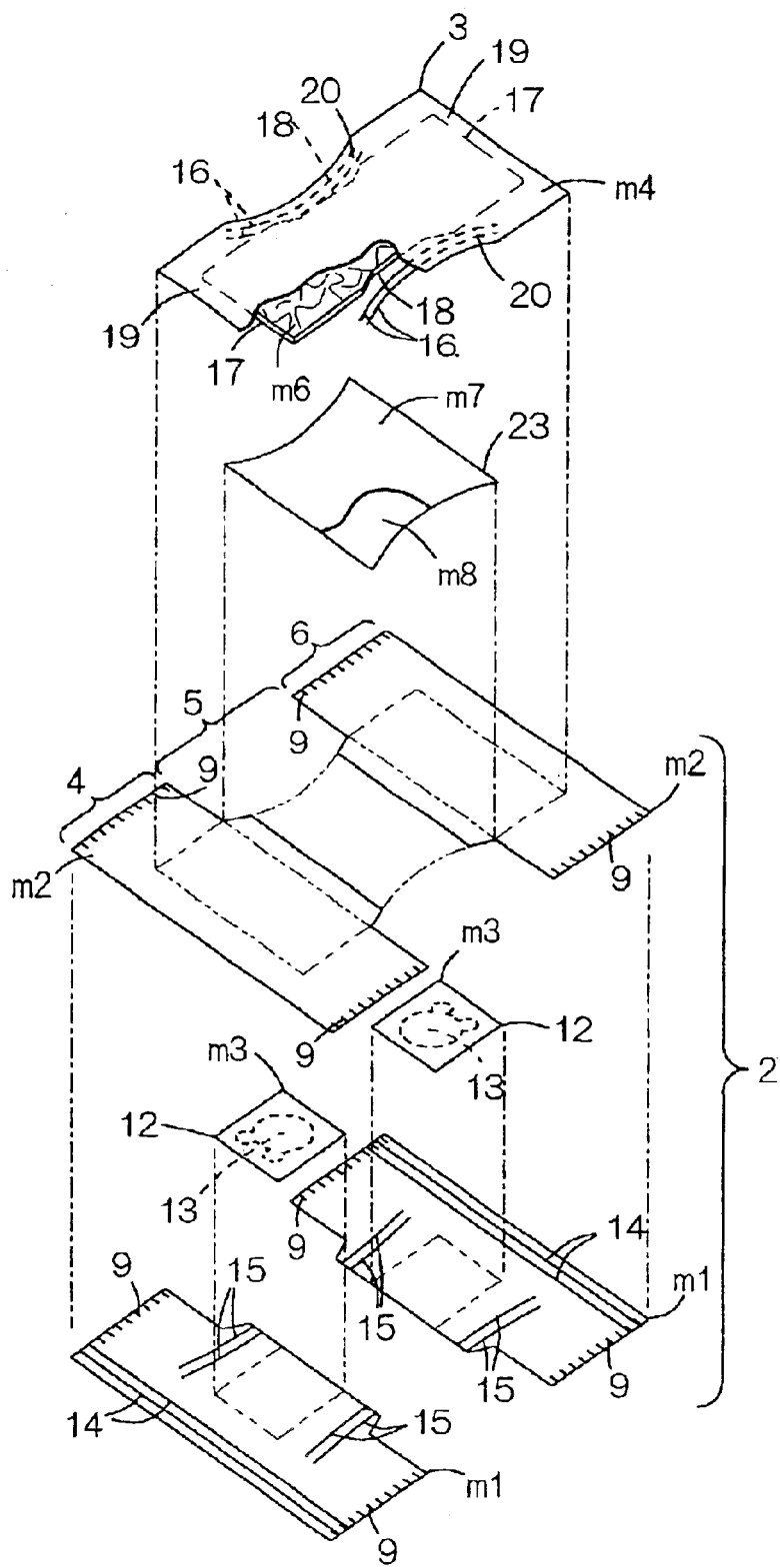
FIG. 17 is a partially cutaway perspective view showing the embodiment of the article of FIG. 16.

FIG. 16 is a perspective view showing further another embodiment 1D of the article adopting the process according to this invention and FIG. 17 is a partially cutaway perspective view showing the embodiment 1D of the article of FIG. 16. In FIGS. 16 and 17, a waist-circumferential direction is indicated by an arrow X, a longitudinal direction is indicated by an arrow Y and a leg-circumferential direction is indicated by an arrow Z (only in FIG. 16).

The article 1D comprises a substantially liquid-impervious composite nonwoven fabric layer 2 (i.e., composite web), a liquid-impervious composite sheet 23 joined to the inner surface of the nonwoven fabric layer 2 and a liquid-absorbent panel 3 joined to the inner surfaces of the nonwoven fabric layer 2 and the sheet 23, respectively.

The article 1D is composed of front and rear waist regions 4, 6 opposed to each other, a crotch region 5 extending between these waist regions 4, 6, end flaps 7 extending in the waist-circumferential direction and side flaps 8 extending in the longitudinal direction and in the leg-circumferential direction.

The article 1D is of pull on-type having a waist-opening 10 and a pair of leg-openings 11. In the article 1D, the composite nonwoven fabric layer 2 lies in the front and rear waist regions 4, 6 and the composite sheet 23 lies in the crotch region 5.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly secured to the side flaps 8.

The front and rear waist regions 4, 6 are provided in respective middle zones thereof as viewed in the waist-circumferential direction with the respective halves of an indication sheet 12 each having illustration of a bear's face (indicator element 13) printed thereon. The indication sheet 12 is formed by a breathable and liquid-impervious plastic film m3.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web). An inner surface of the first fibrous nonwoven fabric layer m1 and an outer surface of the second fibrous nonwoven fabric layer m2 are joined together by means of a hot melt adhesive (not shown). The adhesive is intermittently applied on the first fibrous nonwoven fabric layer m1 over its whole inner surface.

The indication sheet 12 and the first and second stretchable elastic members 14, 15 are interposed between the first fibrous nonwoven fabric layer m1 and the second fibrous nonwoven fabric layer m2 and joined to an inner surface of the nonwoven fabric layer m1. The indication sheet 12 is thus not joined to the second fibrous nonwoven fabric layer m2.

The composite sheet 23 comprises a breathable and liquid-impervious plastic film m7 and a breathable hydrophobic fibrous nonwoven fabric layer m8 placed upon each other. The composite sheet 23 presents an hourglass-like planar shape and is smaller than the panel 3 and covers an under surface of a core m6 in the crotch region 5 (See FIG. 17). The composite sheet 23 is joined to an inner surface of the nonwoven fabric layer m2 by means of the hot melt adhesive (not shown). The film m7 and the nonwoven fabric layer m8 are joined together by means of the hot melt adhesive (not shown).

The panel 3 comprises a breathable hydrophobic fibrous nonwoven fabric layer m4 lying on the side facing the wearer's body and the liquid-absorbent core m6 joined to an inner surface of a nonwoven fabric layer m4. The nonwoven fabric layer m4 is slightly larger than an upper surface of the core m6 and covers this upper surface over its whole area. The nonwoven fabric layer m4 is slightly larger than the upper surface of the core m6 and covers the upper surface of the core m6 over its whole area. The nonwoven fabric layer m4 has longitudinally opposite margins 19 extending outward beyond the longitudinally opposite ends 17 of the core m6 and transversely opposite lateral margins 20 extending outward from transversely opposite side edges 18 of the core m6. The third stretchable elastic members 16 are secured to those lateral margins 20 of the nonwoven fabric layer m4 by means of the hot melt adhesive (not shown).

In the panel 3, the longitudinally opposite margins 19 and the transversely opposite lateral margins 20 of the nonwoven fabric layer m4 lying in the front and rear waist regions 4, 6, respectively, are joined to the inner surface of the film m7 by means of the hot melt adhesive (not shown). The under surface of the core m6 and the lateral margins 20 of the nonwoven fabric layer m4 are joined to an inner surface of the film m7 by means of the hot melt adhesive (not shown). The adhesive is intermittently applied on the nonwoven fabric layer m4 over its whole inner surface as well as on the film m7 over its whole inner and outer surfaces.

The end flaps 7 are defined by portions of the nonwoven fabric layers m1, m2, m4 extending outward beyond the longitudinally opposite ends 17 of the core m6. The side flaps 8 are defined by portions of the nonwoven fabric layers m1, m2, m4, m8 and the film m7 extending outward in the waist-circumferential direction beyond the transversely opposite side edges 18 of the core m6.

Figure 18:
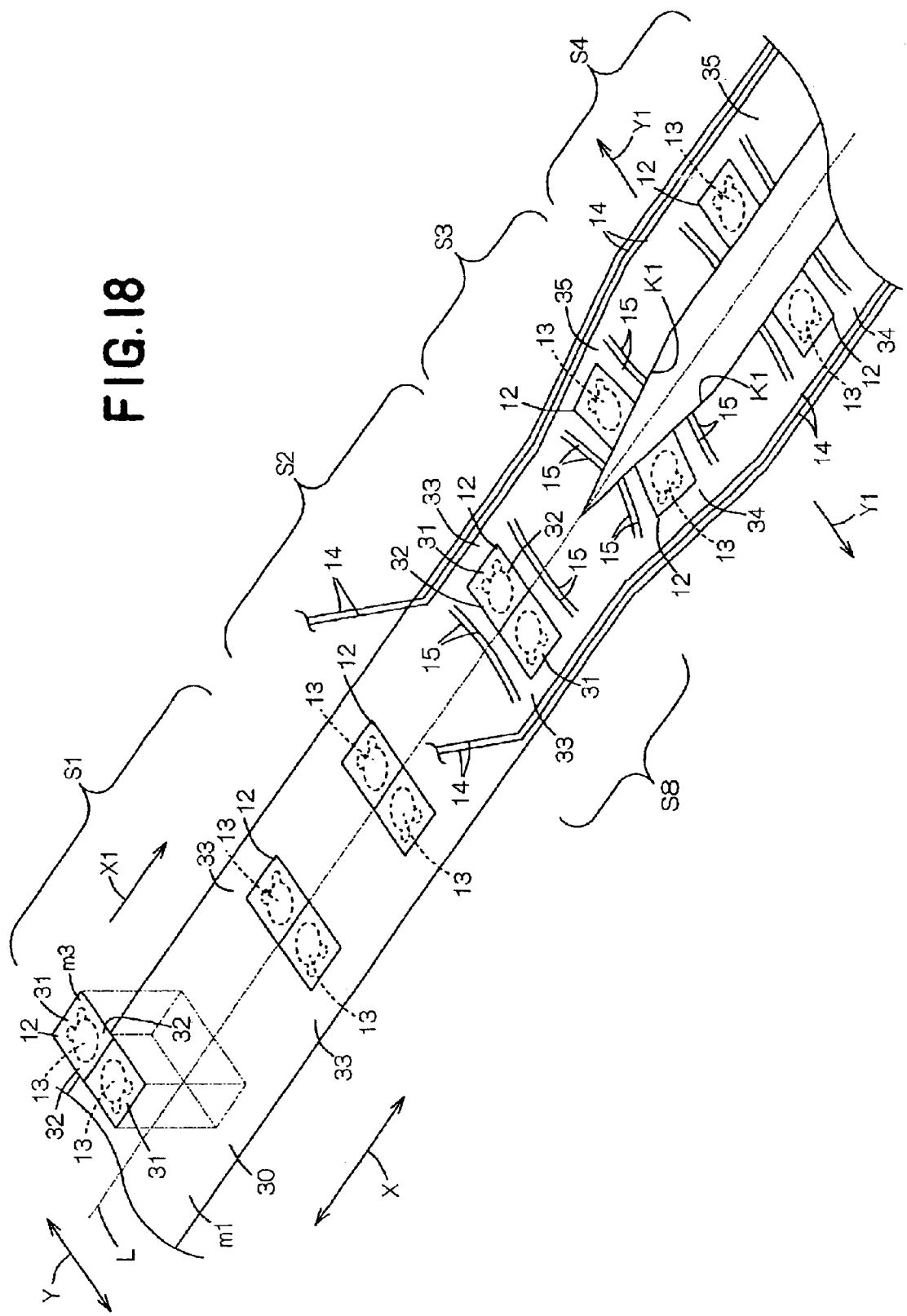
FIG. 18 is a perspective view schematically illustrating further another embodiment of the process for placing the indicator element.
Figure 19:
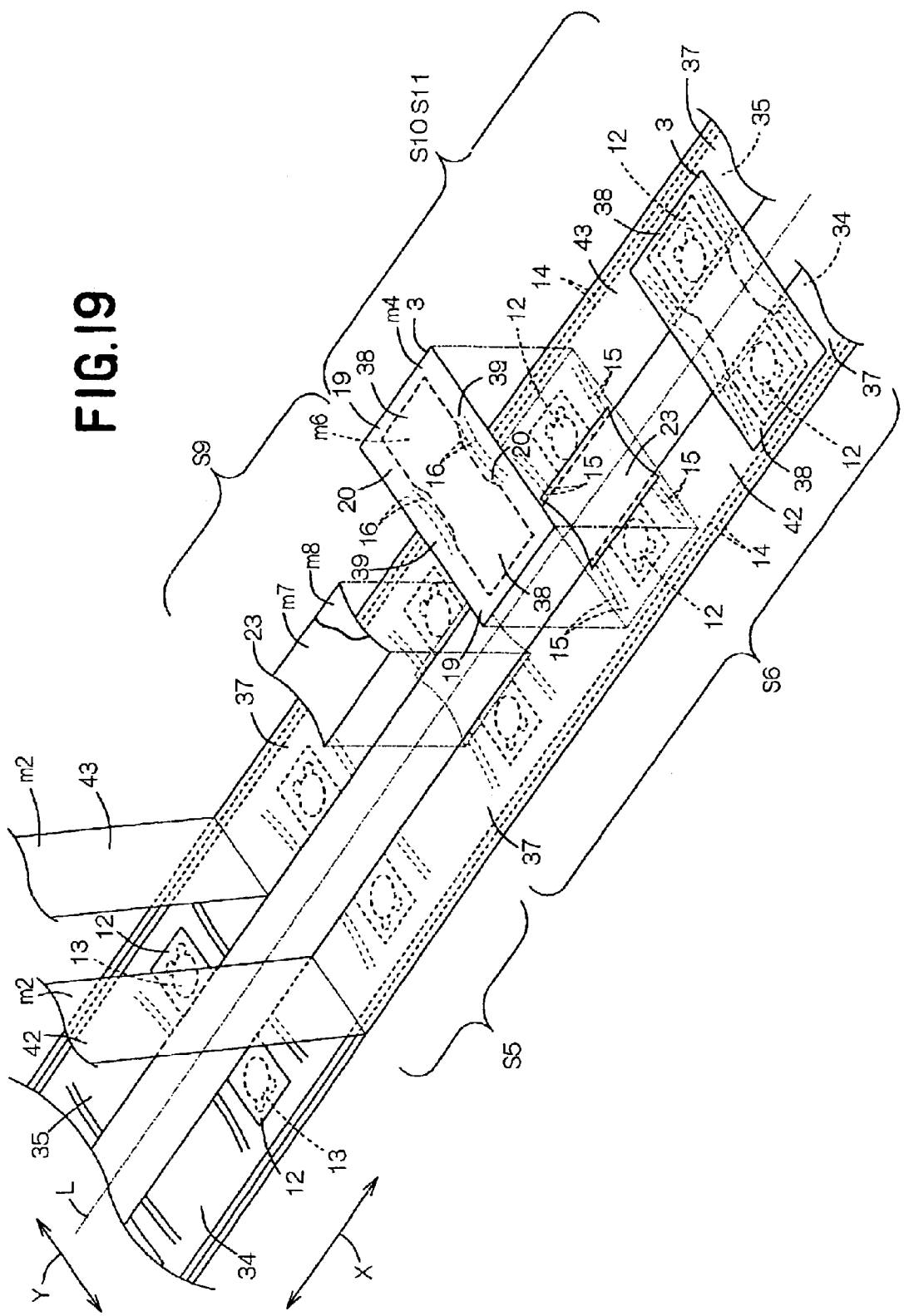
FIG. 19 is a perspective view schematically illustrating the steps subsequent to the steps in the process illustrated in FIG. 18.
Figure 20:
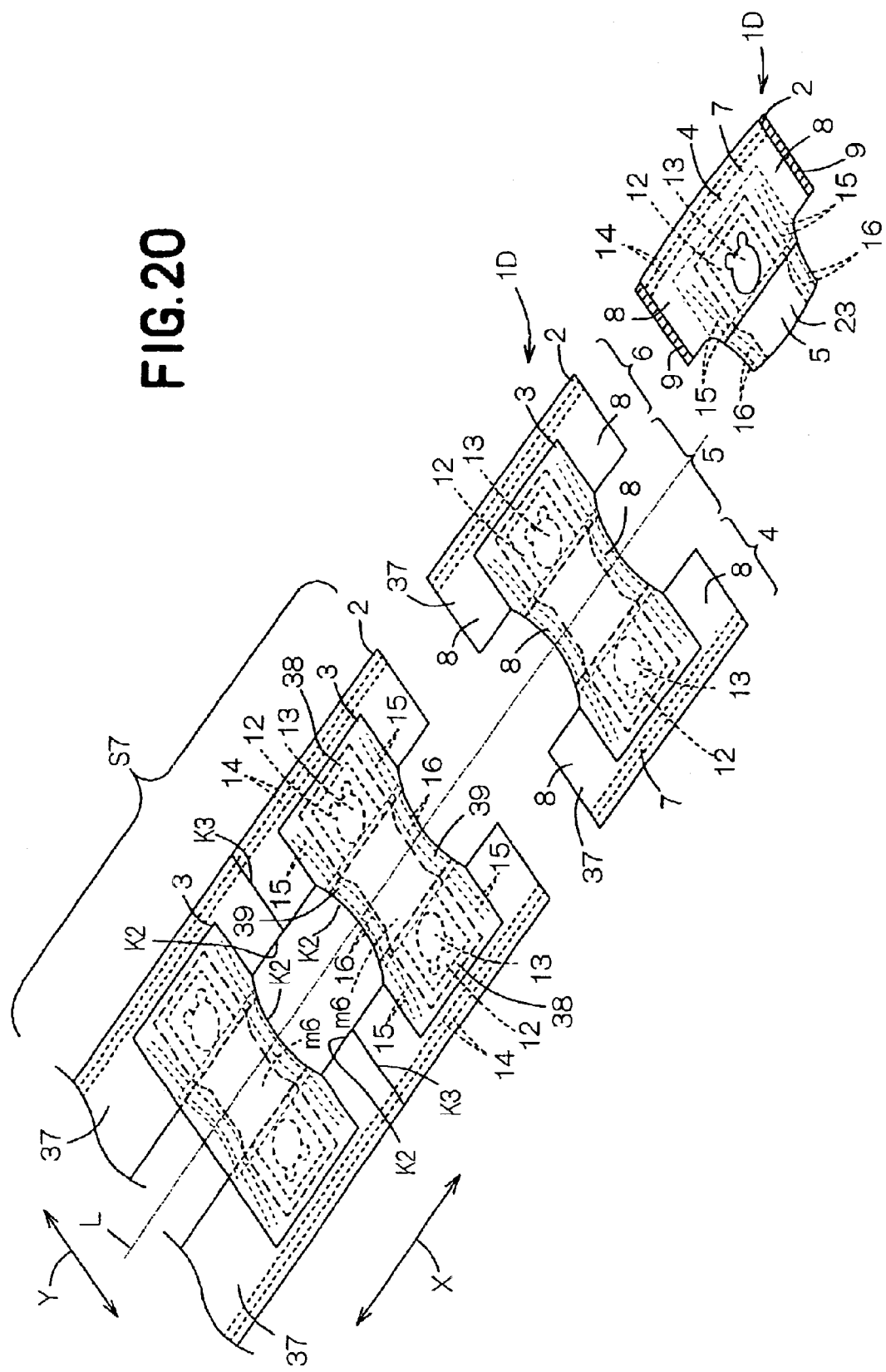
FIG. 20 is a perspective view schematically illustrating the steps subsequent to the steps in the process illustrated in FIG. 19.

FIG. 18 is a perspective view schematically illustrating further another embodiment of the process for placement of the indicator elements, FIG. 19 is a perspective view schematically illustrating the steps subsequent to the steps in the process illustrated in FIG. 18 and FIG. 19 is a perspective view schematically illustrating the steps subsequent to the steps in the process illustrated in FIG. 18. Referring to these Figures, a machine direction (MD) is indicated by an arrow X and a cross direction (CD) is indicated by an arrow Y. According to this process, the article 1D of FIG. 16 is made and the indicator element is formed in the front and rear waist regions 4, 6 of the article 1D through successive steps as will be described.

Step S1: In the step S1, a plurality of the indication sheets 12 each having a pair of indicator elements 13 are successively fed onto an upper surface (i.e., inner surface) of an outer web 30 continuously running in the MD. The indication sheets 12 are placed on the upper surface of the outer web 30 so as to be spaced apart one from another by a predetermined dimension in the MD. The indicator elements 13 are a pair of illustrated bear's faces arranged side by side. These illustrated bear's faces are in mirror image relationship with each other.

The outer web 30 is formed by the breathable hydrophobic fibrous nonwoven fabric layer m1 (i.e., the first fibrous nonwoven fabric layer). The indication sheet 12 is formed by the breathable and liquid-impervious plastic film m3.

Step S2: In this step S2, the indication sheet 12 is joined to the upper surface of the outer web 30 with the individual indicator elements 13 placed on both sides of the imaginary line L. The indication sheet 12 is joined to the outer web 30 by means of the hot melt adhesive (not shown) intermittently applied on the outer web 30 over its whole upper surface.

In this step S2, a plurality of the first stretchable elastic members 14 (waist elastic members) continuously extending in the MD are secured in a stretched state to the upper surface of the outer web 30 while a plurality of the second stretchable elastic members 15 (leg elastic members) extending in the CD are secured in a stretched state to the upper surface of the outer web 30 (step S8).

Step S3: In the step S3, the outer web 30, the indication sheet 12 and the elastic members 15 are cut along a cutting line K1 extending along the imaginary line L and bisected in the CD.

In the step S3, the outer web 30 is divided into first and second outer webs 34, 35 and at the same time each pair of the indicator elements 13 is divided into the individual indicator elements 13.

Step S4: In the step S4, the first outer web 34 and the second outer web 35 are separated from each other by a predetermined dimension in the CD indicated by an arrow Y1 with a pair of halves bisected from the indication sheet 12 being aligned with each other in the CD.

Step S5: In the step S5, an under surface (i.e., an outer surface) of a first inner web 42 continuously running in the MD is placed upon an upper surface of the first outer web 34, and an under surface (i.e., an outer surface) of a second inner web 43 continuously running in the MD is placed upon an upper surface of the second outer web 35. Then, the first outer web 34 and the first inner web 43 are joined together while the second outer web 35 and the second inner web 43 are joined together.

In this step S5, the first and second outer webs 34, 35 cooperate with the first and second inner web 42, 43 to form a composite web 37 (i.e., the composite nonwoven fabric layer 2). The indication sheets 12 and the inner webs 42, 43 are not joined. Each of the first and second inner webs 42, 43 is formed by the breathable hydrophobic fibrous nonwoven fabric layer m2 (i.e., the second fibrous nonwoven fabric layer).

Step S6: In the step S6, a plurality of the composite sheets 23 are successively fed onto respective upper surfaces (i.e., inner surfaces) of the first and second inner webs 42, 43. Thus the composite sheets 23 are placed on the respective upper surfaces of the inner webs 42, 43 so as to be spaced apart one from another by a predetermined dimension in the MD (step S9).

Each of the composite sheets 23 bridges the halves of the associated indication sheet 12 having been bisected and spaced apart from each other so as to overlay these halves of the indication sheet 12. The composite sheets 23 are placed on the upper surfaces of the first and second inner webs 42, 43 so as to be spaced apart one from another in the MD by a predetermined dimension. Then, the under surface of the composite sheet 23 is joined to the upper surfaces of these inner webs 42, 43 (step S10). The composite sheet 23 and the inner webs 42, 43 are joined together by means of the hot melt adhesive (not shown) intermittently applied on a part of nonwoven fabric layer m8 which will be described later.

In the step S6, a plurality of the liquid-absorbent panels 3 are successively fed onto the upper surface of the composite sheet 23. The transversely opposite margins 38 of the panel 3 are positioned on the indication sheet 12. Thereafter, the under surface of the panel 3 is joined to the upper surface of the composite sheet 23 by means of the hot melt adhesive (not shown) (step S11). At the same time, the transversely opposite margins 38 of the panel 3 are joined to the respective upper surfaces of the first and second inner webs 42, 43 by means of the hot melt adhesive (not shown).

Each of the composite sheets 23 presents an hourglass-like planar shape and comprises the breathable and liquid-impervious plastic film m7 and the breathable hydrophobic fibrous nonwoven fabric layer m8. The panel 3 comprises the breathable hydrophobic fibrous nonwoven fabric layer m4 and the liquid-absorbent core m6 underlying the nonwoven fabric layer m4 (See FIG. 17). The panel 3 is provided along its lateral margins 39 with the stretchable elastic members 16 (leg elastic members) extending in the CD. These stretchable elastic members 16 are secured in a stretched state to the panel 3.

In the panel 3, the under surface of the nonwoven fabric layer m4 is joined to an upper surface of the core m6 by means of the hot melt adhesive (not shown). The longitudinally opposite margins 19 and the transversely opposite lateral margins 20 of the nonwoven fabric layer m4 are joined to the upper surfaces of the inner webs 42, 43 as well as to an upper surface of the film m7 by means of the hot melt adhesive (not shown). The under surface of the core m6 is joined to the upper surface of the film m7 by means of the hot melt adhesive (not shown). The adhesive is intermittently applied on the nonwoven fabric layer m4 over its whole under surface and on the film m7 over its whole upper and under surfaces.

The process may be implemented without departing the scope of the invention so that the composite sheets 23 are fed onto the upper surfaces of the inner webs 42, 43 so as to be spaced apart one from another by a predetermined dimension in the MD and/or the under surface of the composite sheet 23 is joined to the upper surfaces of the inner webs 42, 43 in the step S5.

Step S7: In the step S7, the composite web 37 and the opposite lateral margins 39 of the panels 3 are cut along the lines K2, K3 extending across the composite web 37 between each pair of the adjacent panels 3.

Between the halves of the composite web 37 having been separated in the CD from each other, each of the substantially square regions is cut out from assembly of the composite web 37 and the opposite lateral margins 39 of the panels 3 along the cutting line K2 of which a pair of transverse sections describe circular arcs being convex toward the core m6 and thereby cutouts destined to form a periphery of the leg-opening are obtained. At the same time, the composite web 37 is cut along the cutting line K3 rectilinearly extending in the CD. Those regions are cut out from the assembly of the composite web 37 and the opposite lateral margins 39 of the panel 3 in this manner to obtain a plurality of the individual articles 1D.

The article 1D obtained in this manner has a substantially hourglass-like planar shape to define, as viewed in the CD of the web 37, the front waist region 4, the rear waist region 6 and the crotch region 5 extending between these waist regions 4, 6.

After the composite web 37 has been cut and the transversely opposite lateral margins 39 of the respective panels 3 have been trimmed, the composite web 37 and the associated panel 3 are folded along the imaginary line L with the panel 3 inside and the front waist region 4 and the rear waist region 6 both formed by the composite web 37 are placed upon each other. Then, these front and rear waist regions 4, 6 are joined together by means of the welding lines 9 to obtain the pull on-type article.

Figure 21:
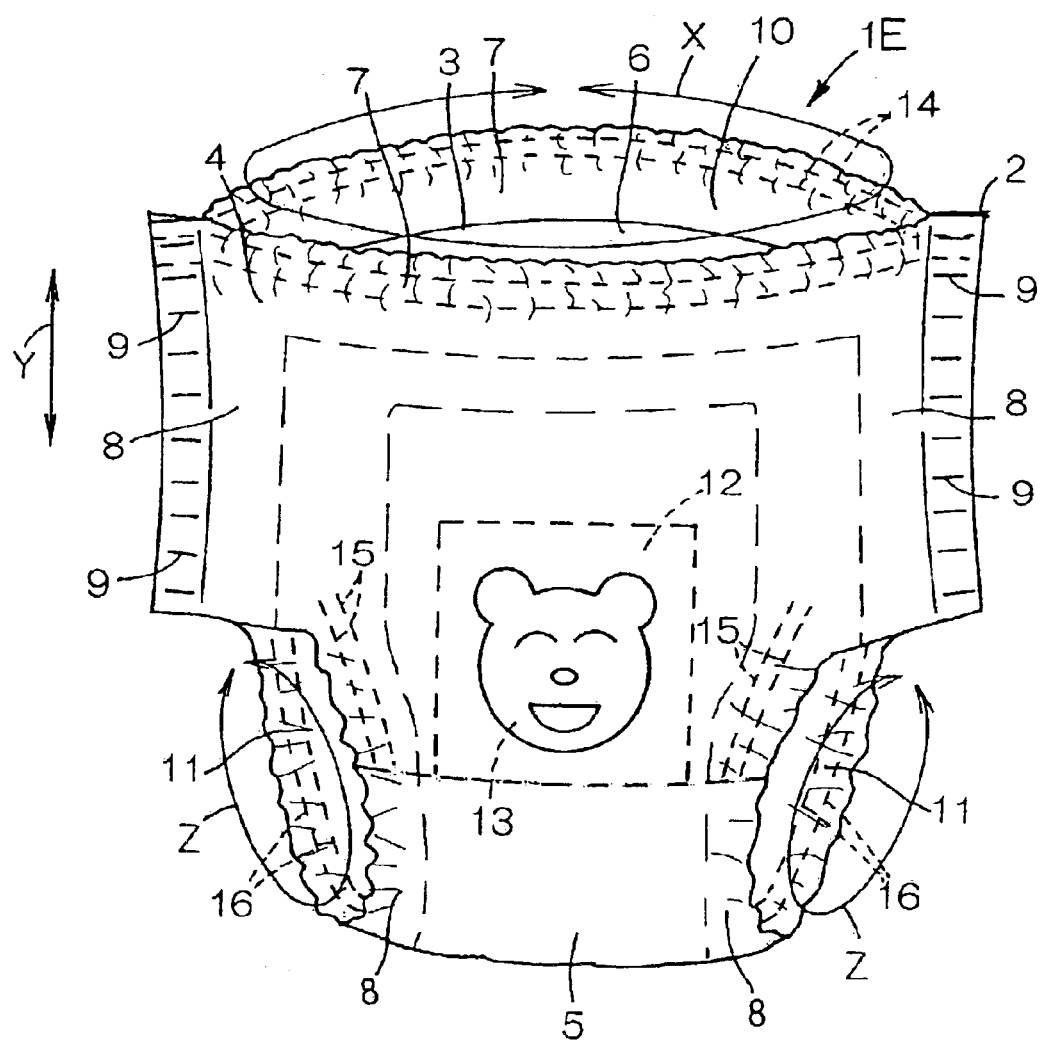
FIG. 21 is a perspective view showing an alternative embodiment of the article adopting the process according to this invention.
Figure 22:
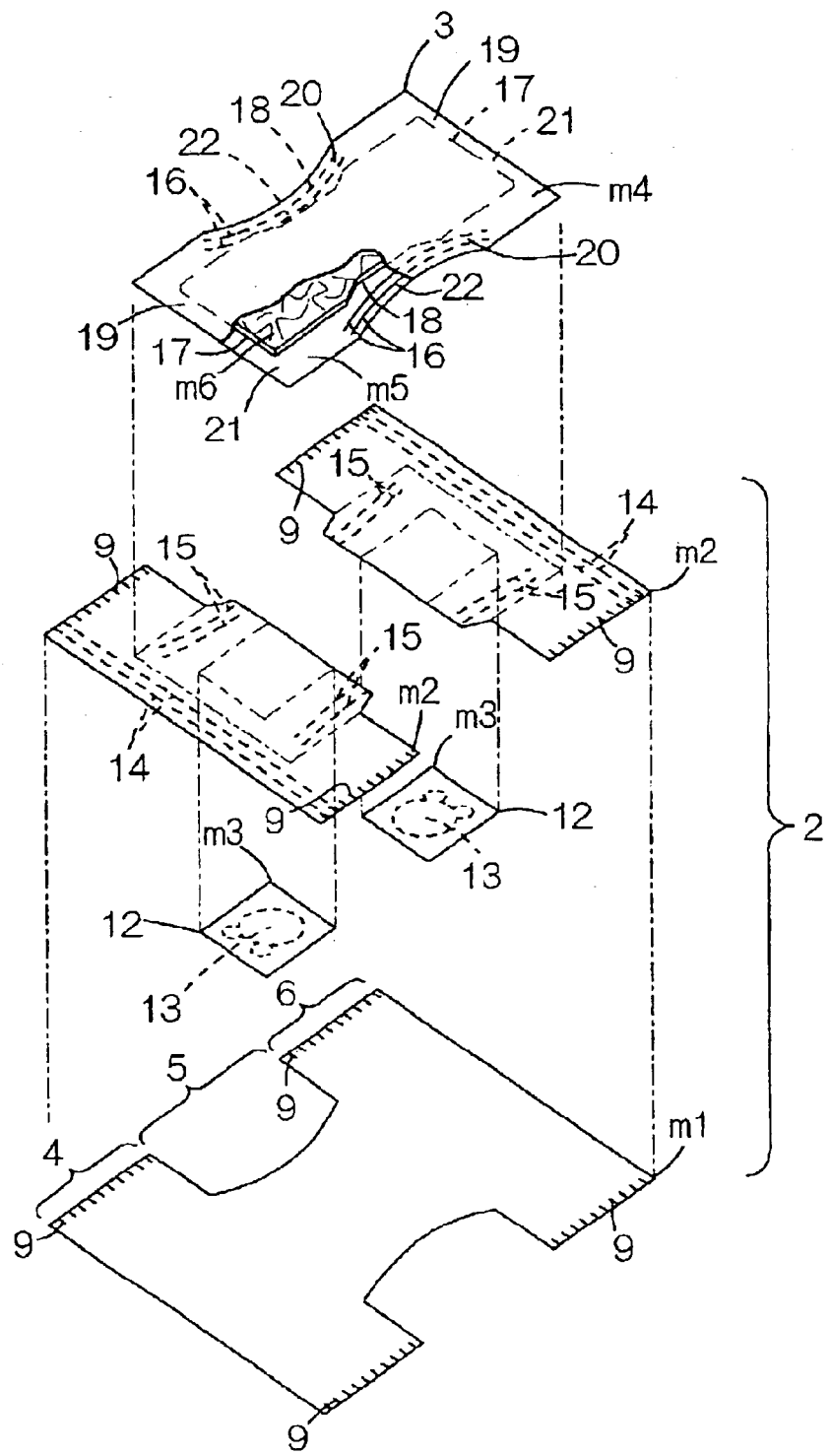
FIG. 22 is a partially cutaway perspective view showing the embodiment of the article of FIG. 21.

FIG. 21 is a perspective view showing further alternative embodiment 1E of the article adopting the process according to this invention and FIG. 22 is a partially cutaway perspective view showing the embodiment 1E of the article of FIG. 21. In FIGS. 21 and 22, a waist-circumferential direction is indicated by an arrow X, a longitudinal direction is indicated by an arrow Y and a leg-circumferential direction is indicated by an arrow Z (only in FIG. 21).

The article 1E comprises a substantially liquid-impervious composite nonwoven fabric layer 2 (i.e., a composite web) and the liquid-absorbent panel 3 joined to the inner surface of the composite nonwoven fabric layer 2. The article 1E has front and rear waist regions 4, 6 opposed to each other, a crotch region 5 extending between these waist regions 4, 6, end flaps 7 extending in the waist-circumferential direction and side flaps 8 extending in the longitudinal direction as well as in the leg-circumferential direction. The article 1E is of pull on-type having a waist-opening 10 and a pair of leg-openings 11.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly secured to the side flaps 8.

The front and rear waist regions 4, 6 are provided in respective middle zones thereof as viewed in the waist-circumferential direction with the respective halves of an indication sheet 12 each having an illustration of a bear's face (indicator element 13) printed thereon. The indication sheet 12 is formed by a breathable and liquid-impervious plastic film m3.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web) lying on an inner surface of the nonwoven fabric layer m1. Of the composite nonwoven fabric layer 2, the first fibrous nonwoven fabric layer m1 lies in the front and rear waist regions 4, 6 as well as in the crotch region 5 while the second fibrous nonwoven fabric layer m2 lies in the front and rear waist regions 4, 6. An inner surface of the first fibrous nonwoven fabric layer m1 and an outer surface of the second fibrous nonwoven fabric layer m2 are joined together by means of a hot melt adhesive (not shown). The adhesive is intermittently applied on the second fibrous nonwoven fabric layer m2 over its whole inner surface.

The indication sheet 12 and the first and second stretchable elastic members 14, 15 are interposed between the first fibrous nonwoven fabric layer m1 and the second fibrous nonwoven fabric layer m2 and joined to the inner surface of the nonwoven fabric layer m2. The indication sheet 12 is thus not joined to the first fibrous nonwoven fabric layer m1.

The panel 3 comprises the breathable hydrophobic fibrous nonwoven fabric layer m4 lying on the side facing the wearer's body, a breathable and liquid-impervious plastic film m5 facing away from the wearer's body and a liquid-absorbent core m6 interposed between the nonwoven fabric layer m4 and the film m5. An outer surface of the film m5 constituting the panel 3 is joined to the respective inner surfaces of the first and second fibrous nonwoven fabric layers m1, m2 by means of the hot melt adhesive (not shown).

The nonwoven fabric layer m4 is slightly larger than an upper surface of the core m6 and covers this upper surface over its whole area. The film m5 is slightly larger than an under surface of the core m6 and covers this under surface of the core m6 over its whole area. The nonwoven fabric layer m4 and the film m5 respectively have the longitudinally opposite margins 19, 21 extending outward beyond longitudinally opposite ends 17 of the core m6 and transversely opposite lateral margins 20, 22 extending outward from transversely opposite side edges 18 of the core m6.

The nonwoven fabric layer m4 has its inner surface joined to the upper surface of the core m6 by means of the hot melt adhesive (not shown). The film m5 has its inner surface joined to the under surface of the core m6 by means of the hot melt adhesive (not shown). The adhesive is intermittently applied on the nonwoven fabric layer m4 over its whole inner surface as well as on the film m5 over its whole inner and outer surfaces.

The nonwoven fabric layer m4 and the film m5 are joined together along the longitudinally opposite margins 19, 21 and the transversely opposite lateral margins 20, 22 thereof. The third stretchable elastic members 16 are interposed between the nonwoven fabric layer m4 and the film m5 and secured to the transversely opposite lateral margins 20, 22 of these nonwoven fabric layer m4 and film m5, respectively.

The end flaps 7 are defined by portions of the nonwoven fabric layers m1, m2, m4 and the film m5 extending outward beyond the longitudinally opposite ends 17 of the core m6. The side flaps 8 are defined by portions of the nonwoven fabric layers m1, m2, m4 and the film m5 extending outward in the waist-circumferential direction beyond the transversely opposite side edges 18 of the core m6.

The panel 3 may be also constituted from the breathable hydrophobic fibrous nonwoven fabric layer m4 and the liquid-absorbent core m6 joined to the inner surface of the nonwoven fabric layer m4 in the absence of the film m5. In this case, the lower surface of the nonwoven fabric layer m4 extending along its longitudinally opposite margins 19 as well as its transversely opposite lateral margins 20 and the under surface of the core m6 are joined to the respective inner surfaces of the first and second fibrous nonwoven fabric layer m1, m2.

Figure 23:
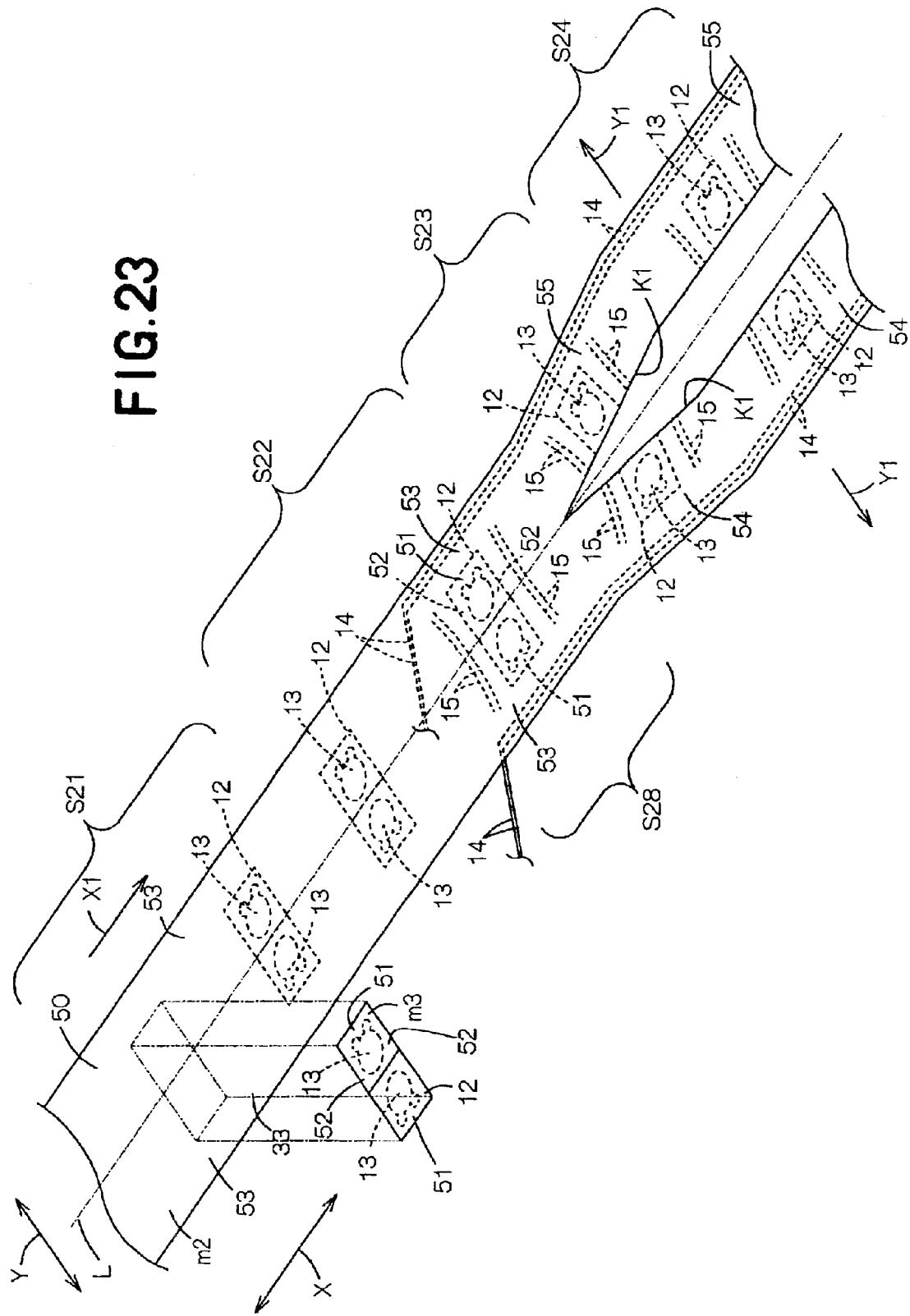
FIG. 23 is a perspective view schematically illustrating an alternative embodiment of the process for placing the indicator element.
Figure 24:
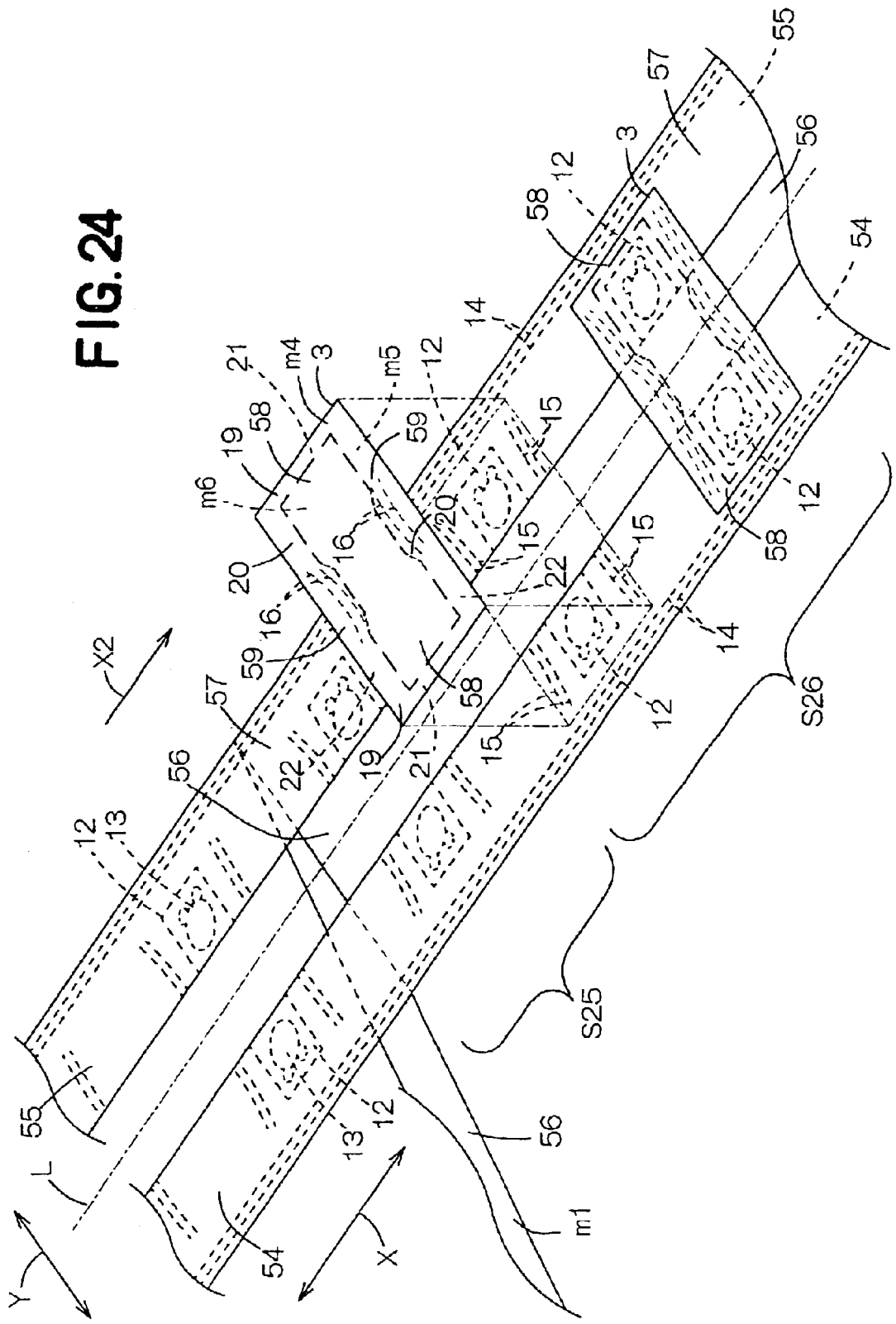
FIG. 24 is a perspective view schematically illustrating the steps subsequent to the steps in the process illustrated in FIG. 23.
Figure 25:
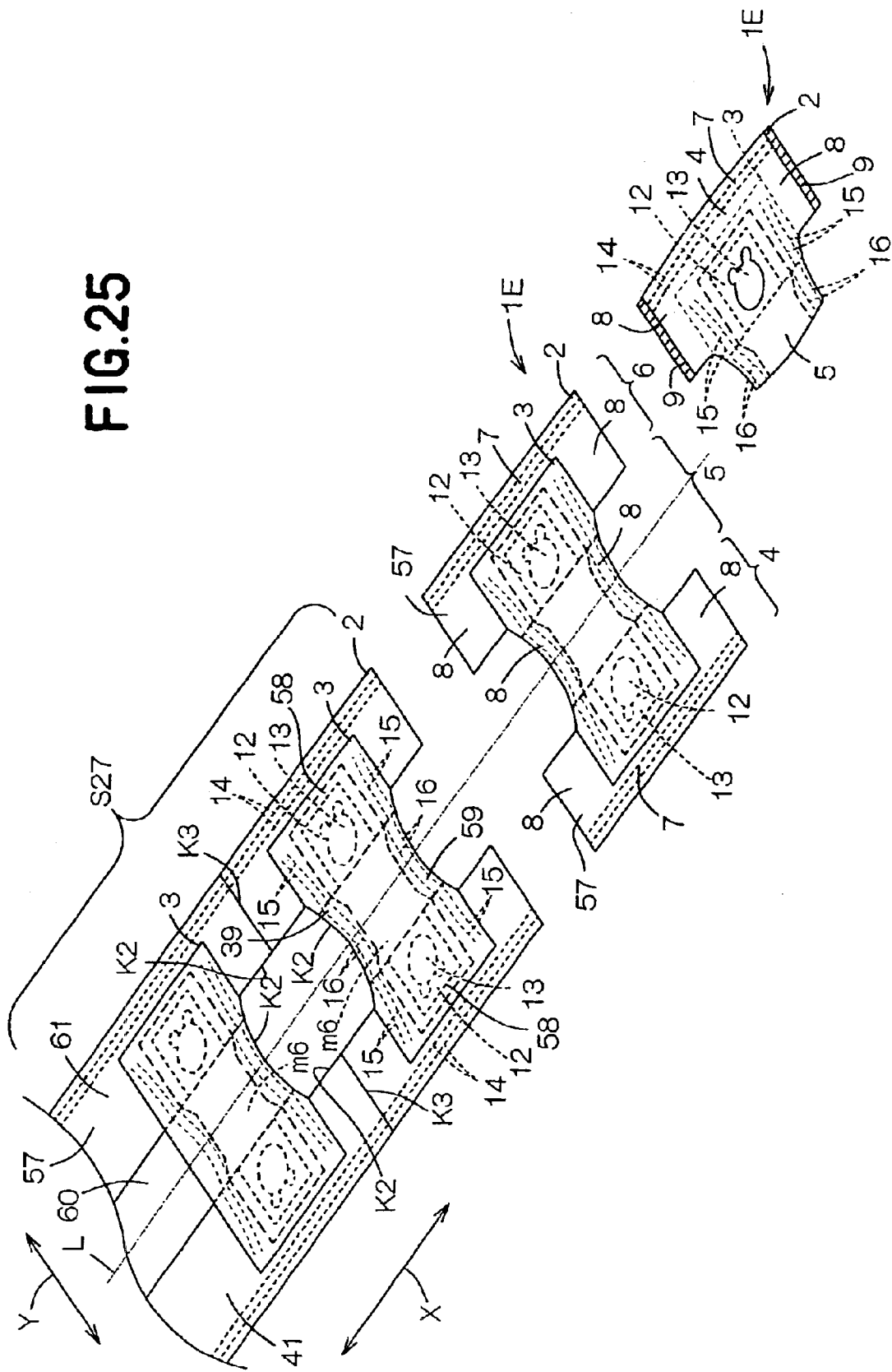
FIG. 25 is a perspective view schematically illustrating the steps subsequent to the steps in the process illustrated in FIG. 24.

FIG. 23 is a perspective view schematically illustrating further alternative embodiment of the process for placing the indicator element, FIG. 24 is a perspective view schematically illustrating the steps subsequent to the steps in the process illustrated in FIG. 23 and FIG. 25 is a perspective view schematically illustrating the steps subsequent to the steps in the process illustrated in FIG. 24. Referring to these Figures, a longitudinal direction is indicated by an arrow X and a transverse direction is indicated by an arrow Y. According to this process, the article 1E of FIG. 21 is made and the indicator element is formed in the front and rear waist regions 4, 6 of the article 1E through successive steps as will be described.

Step S21: In the step S21, a plurality of the indication sheets 12 each having a pair of indicator elements 13 are successively fed under an inner web 50 continuously running in the MD.

The indication sheets 12 are placed under the inner web 50 so as to be spaced apart one from another by a predetermined dimension in the MD. The indicator elements 13 are a pair of illustrated bear's faces arranged side by side in mirror image relationship with each other.

Each of the indication sheets 12 is in form of a rectangle having long sides extending in the CD and contoured by transversely opposite ends 51 extending in the MD and longitudinally opposite side edges 52 extending in the CD. A transverse dimension of the indication sheet 12 is smaller than that of the outer web 50, so the ends 51 thereof lie inside the side edges 53 of the inner web 50.

The inner web 50 is formed by the breathable hydrophobic fibrous nonwoven fabric layer m2 (i.e., the second fibrous nonwoven fabric layer). The indication sheet 12 is formed by the breathable and liquid-impervious plastic film m3.

Step S22: In the step S22, the indication sheet 12 is joined to the under surface of the inner web 50 with the individual indicator elements 13 placed on both sides of the imaginary line L bisecting the inner web 50. The indication sheet 12 is joined to the inner web 50 by means of the hot melt adhesive (not shown) intermittently applied on the inner web 50 over its whole under surface.

In this step S22, a plurality of the first stretchable elastic members 14 (waist elastic members) continuously extending in the MD are secured in a stretched state to the under surface of the inner web 50 along its transversely opposite lateral margins 53 while a plurality of second stretchable elastic members 15 (leg elastic members) extending in the CD are secured in a stretched state to the inner web 50 over its whole under surface (step S28).

The first stretchable elastic members 14 extend outside the respective lateral margins 51 of the indication sheet 12. The second stretchable elastic members 15 extend outside the transversely opposite side edges 52 of the indication sheet 12. These first and second stretchable elastic members 14, 15 are joined to the under surface of the inner sheet 50 by means of the hot melt adhesive.

Step S23: In the step S23, the inner web 50, the indication sheet 12 and the elastic members 15 are cut along a cutting line K1 extending along the imaginary line L and bisected in the CD.

In the step S23, the inner web 50 is divided into first and second inner webs 54, 55 and at the same time each pair of the indicator elements 13 is divided into the individual indicator elements 13. Of the paired indicator elements 13 on the indication sheet 12, the one lies under the first inner web 54 and the other lies under the second inner web 55.

Step S24: In the step S24, the first and second inner webs 54, 55 are separated from each other by a predetermined dimension in the CD indicated by an arrow Y1 with pair of halves bisected from the indication sheet 12 being aligned with each other in the CD.

Step S25: In the step S25, an outer web 56 continuously running in the MD is placed under the first and second inner webs 54, 55 and then these first and second inner webs 54, 55 are joined to the outer web 56 by means of the hot melt adhesive with the indication sheets 12 interposed therebetween.

In this step S25, the first and second inner webs 54, 55 cooperate with the outer web 56 to form a composite web 57 (i.e., the composite nonwoven fabric layer 2). The indication sheets 12 and the outer web 56 are not joined. The outer web 56 is formed by the breathable hydrophobic fibrous nonwoven fabric layer m1 (i.e., the first fibrous nonwoven fabric layer).

The adhesive may be applied also on the outer web 56 over its whole upper surface in addition to the whole under surface of the inner web 50. In this case, the indication sheet 12 is joined to the inner web 50 as well as to the outer web 56.

Step S26: In the step S26, a plurality of the liquid-absorbent panels 3 are successively fed onto an upper surface of the inner web 36. Thus the panels 3 are placed on the upper surface of the inner web 36 so as to be spaced apart one from another in the MD by a predetermined dimension.

In this step S26, the respective upper surfaces of the first and second inner webs 54, 55 are joined to the under surface of the panel 3 while the upper surface of the outer web 56 is joined to the under surface of the panel 3 by means of the hot melt adhesive (not shown) with the transversely opposite margins 58 of the panel 3 positioned on the associated indication sheet 12.

The panel 3 comprises the breathable hydrophobic fibrous nonwoven fabric layer m4, the breathable and liquid-impervious plastic film m5 and the liquid-absorbent core m6 interposed between them (See FIG. 22). The panel 3 is provided along its lateral margins 59 with the third stretchable elastic members 16 (leg elastic members) extending in the CD. These third stretchable elastic members 16 are secured in a stretched state to the panel 3.

In the panel 3, the under surface (i.e., the outer surface) of the film m5 is joined to the respective upper surfaces of the first and second inner webs 54, 55 and to the upper surface of the outer web 56. In the panel 3, the under surface (i.e., the inner surface) of the nonwoven fabric layer m4 is joined to the upper surface of the core m6 while the upper surface (i.e., the inner surface) of the film m5 is joined to the under surface of the core m6, by means of the hot melt adhesive (not shown). The nonwoven fabric layer m4 and the film m5 are joined together along the longitudinally opposite margins 19, 21 and the transversely opposite lateral margins 20, 22 thereof. The third stretchable elastic members 16 are secured to the nonwoven fabric layer m4 as well as to the film m5. The adhesive is intermittently applied on the nonwoven fabric layer m4 over its whole under surface as well as on the film m5 over its whole upper and under surfaces.

The panel 3 may be formed also by the breathable hydrophobic fibrous nonwoven fabric layer m4 and the liquid-absorbent core m6 joined to the inner surface of the nonwoven fabric layer m4. In this case, the respective under surfaces of the portions of the nonwoven fabric layer m4 extending along its longitudinally opposite margins 19 and the transversely opposite lateral margins 20 and the core m6 are joined to the respective upper surfaces of the first and second inner webs 54, 55 as well as to the upper surface of the outer web 56.

Step S27: In the step S27, the composite web 57 and the opposite lateral margins 59 of the panels 3 are cut along the lines K2, K3 extending across the composite web 57 between each pair of the adjacent panels 3.

In a transversely middle zone 60 of the composite web 57, each of the substantially square regions is cut out from assembly of the composite web 57 and the opposite lateral margins 59 of the panels 3 along the cutting line K2 of which a pair of transverse sections describe circular arcs being convex toward the core m6 and thereby cutouts destined to form a periphery of the leg-opening are obtained. At the same time, in the vicinity of the lateral zones 61 of the composite web 57, the composite web 57 is cut along the cutting line K3 rectilinearly extending in the CD. Those regions are cut out from the assembly of the composite web 57 and the opposite lateral margins 59 of the panels 3 in this manner to obtain a plurality of the individual articles 1E.

The article 1E obtained in this manner has a substantially hourglass-like planar shape to define, as viewed in the CD, the front waist region 4, the rear waist region 6 and the crotch region 5 extending between these waist regions 4, 6.

After the composite web 57 has been cut and the transversely opposite lateral margins 59 of the respective panels 3 have been trimmed, the composite web 57 and the associated panel 3 are folded along the imaginary line L with the panel 3 inside and the front waist region 4 and the rear waist region 6 both formed by the composite web 57 are placed upon each other. Then, these front and rear waist regions 4, 6 are joined together by means of the welding lines 9 to obtain the pull on-type article.

Figure 26:
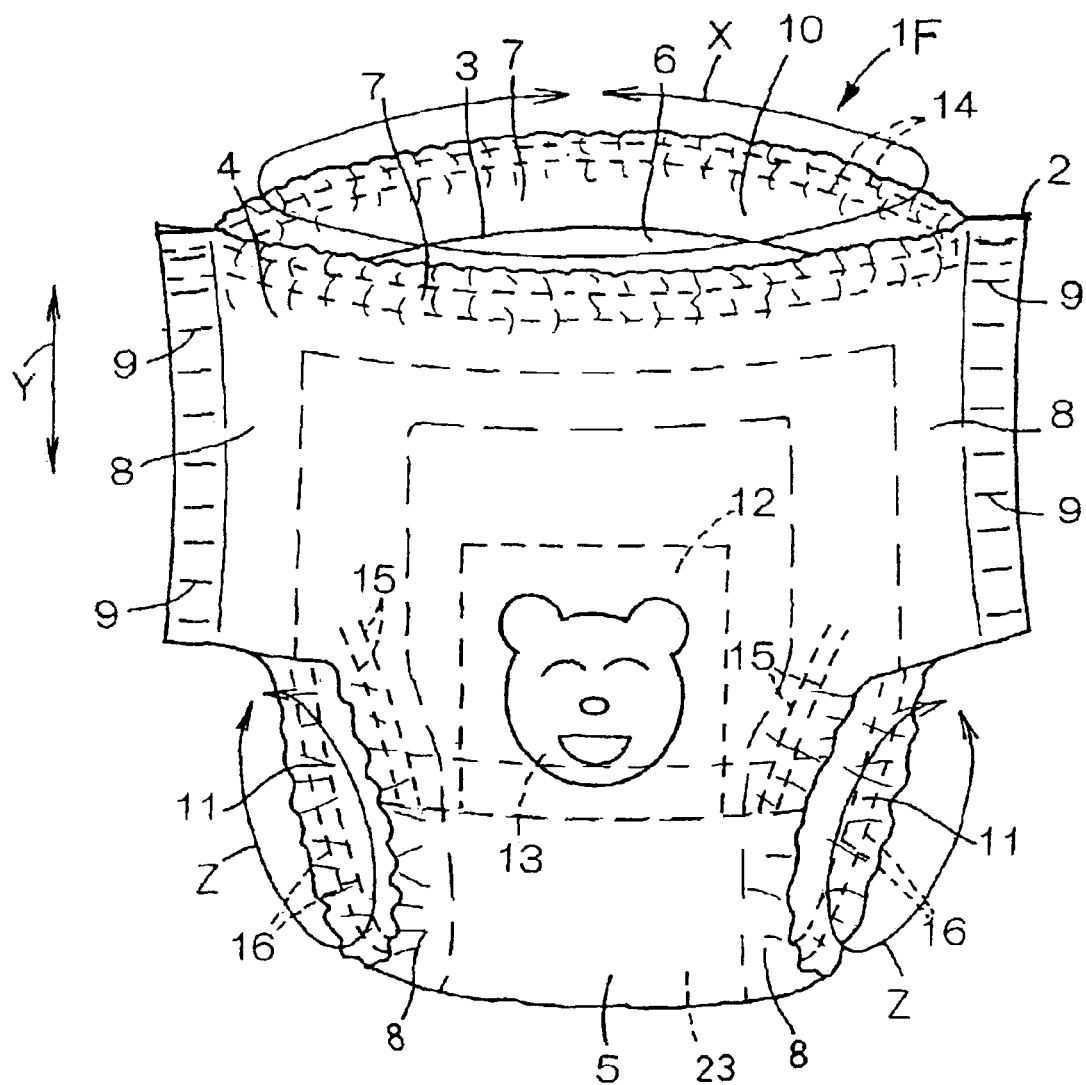
FIG. 26 is a perspective view showing further alternative embodiment of the article adopting the process according to this invention.
Figure 27:
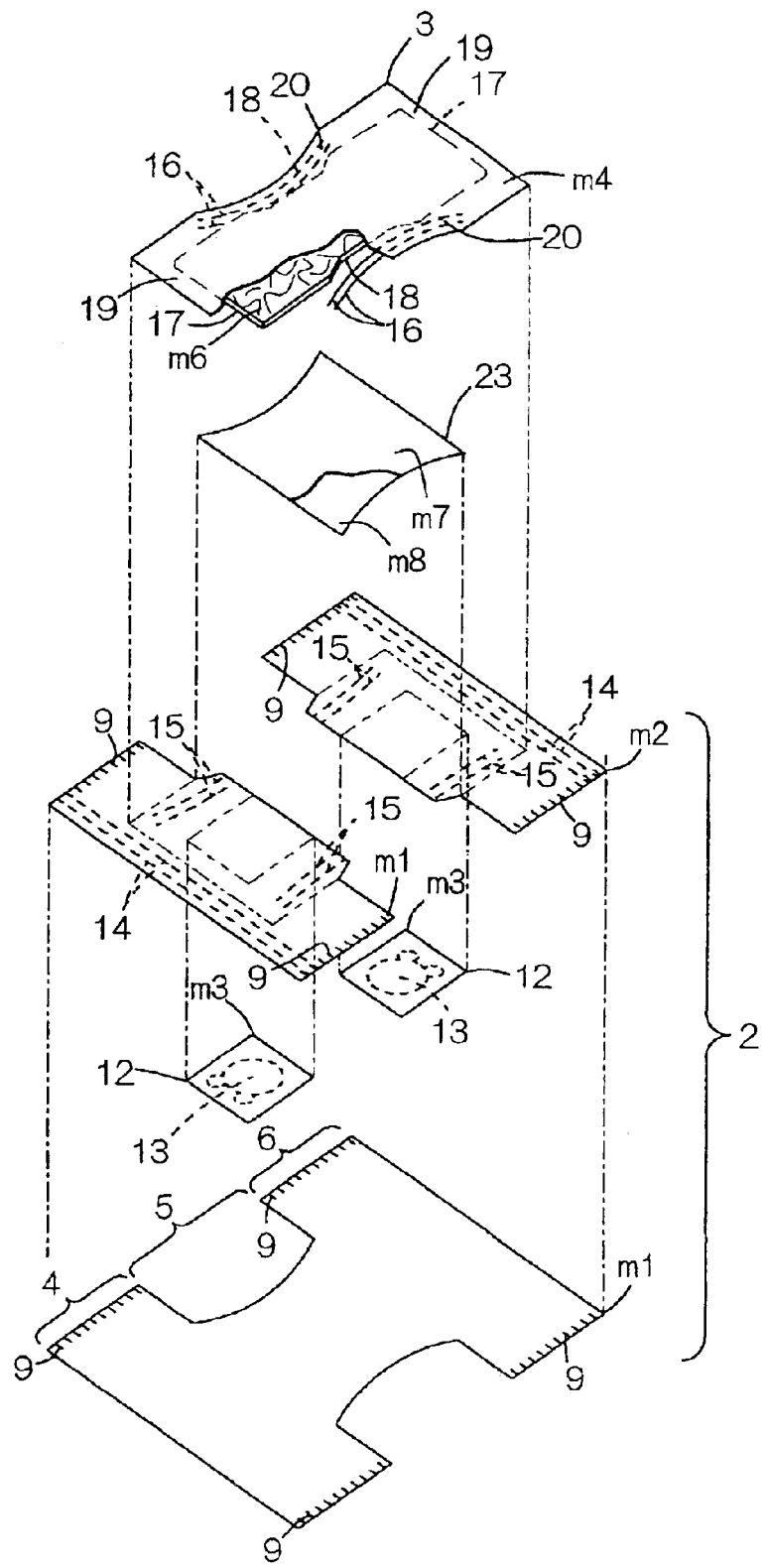
FIG. 27 is a partially cutaway perspective view showing the embodiment of the article of FIG. 26.

FIG. 26 is a perspective view showing further additional embodiment 1F of the article adopting the process according to this invention and FIG. 27 is a partially cutaway perspective view showing the embodiment 1F of the article of FIG. 26. In FIGS. 26 and 27, a waist-circumferential direction is indicated by an arrow X, a longitudinal direction is indicated by an arrow Y and a leg-circumferential direction is indicated by an arrow Z (only in FIG. 26).

The article 1F comprises a substantially liquid-impervious composite nonwoven fabric layer 2 (i.e., a composite web), a liquid-impervious composite sheet 23 joined to the inner surface of the nonwoven fabric layer 2 and the liquid-absorbent panel 3 joined to the respective inner surfaces of these nonwoven fabric layer 2 and the sheet 23.

The article IF has front and rear waist regions 4, 6 opposed to each other, a crotch region 5 extending between these waist regions 4, 6, end flaps 7 extending in the waist-circumferential direction and side flaps 8 extending in the longitudinal direction as well as in the leg-circumferential direction. The article 1F is of pull on-type having a waist-opening 10 and a pair of leg-openings 11.

A plurality of first stretchable elastic members 14 (i.e., waist elastic members) extending in the waist-circumferential direction are contractibly secured to the end flaps 7. A plurality of second stretchable elastic members 15 (i.e., leg elastic members) and a plurality of third stretchable elastic members 16 (i.e., leg elastic members) both extending in the leg-circumferential direction are contractibly secured to the side flaps 8.

The front and rear waist regions 4, 6 are provided in respective middle zones thereof as viewed in the waist-circumferential direction with the respective halves of an indication sheet 12 each having an illustration of a bear's face (indicator element 13) printed thereon. The indication sheet 12 is formed by a breathable and liquid-impervious plastic film m3.

The composite nonwoven fabric layer 2 comprises a breathable hydrophobic first fibrous nonwoven fabric layer m1 (i.e., outer web) and a breathable hydrophobic second fibrous nonwoven fabric layer m2 (i.e., inner web). An inner surface of the first fibrous nonwoven fabric layer m1 and an outer surface of the second fibrous nonwoven fabric layer m2 are joined together by means of a hot melt adhesive (not shown). The adhesive is intermittently applied on the second fibrous nonwoven fabric layer m2 over its whole inner surface.

The indication sheet 12 and the first and second stretchable elastic members 14, 15 are interposed between the first fibrous nonwoven fabric layer m1 and the second fibrous nonwoven fabric layer m2 are joined to the inner surface of the nonwoven fabric layer m2. The indication sheet 12 is thus not joined to the first fibrous nonwoven fabric layer m1.

The composite sheet 23 comprises a breathable and liquid-impervious plastic film m7 and a breathable hydrophobic fibrous nonwoven fabric layer m5 placed upon each other. The composite sheet 23 presents an hourglass-like planar shape and lies in the crotch region 5 of the article 1F. The composite sheet 23 is smaller than that the panel 3 and covers an under surface of the core m6 in the crotch region 5 (See FIG. 27). The film m7 and the nonwoven fabric layer m8 are joined together by means of the hot melt adhesive (not shown).

In the composite nonwoven fabric layer 2 and the composite sheet 23, the inner surfaces of the first and second fibrous nonwoven fabric layers m1, m2 forming the nonwoven fabric layer 2 and an outer surface of the nonwoven fabric layer m8 forming the sheet 23 are joined together by means of the hot melt adhesive (not shown). The composite sheet 23 overlays the indication sheet 12. The adhesive is intermittently applied on the nonwoven fabric layer m8 over its whole inner and outer surfaces.

The panel 3 comprises a breathable hydrophobic fibrous nonwoven fabric layer m4 lying on the side facing the wearer's body and the liquid-absorbent core m6 joined to an inner surface of a nonwoven fabric layer m4. The nonwoven fabric layer m4 is slightly larger than an upper surface of the core m6 and covers the whole upper surface of the core m6 (not shown). The nonwoven fabric layer m4 has longitudinally opposite margins 19 extending outward beyond longitudinally opposite ends 17 of the core m6 and transversely opposite lateral margins 20 extending outward from transversely opposite side edges 18 of the core m6. The third stretchable elastic members 16 are secured to those lateral margins 20 of the nonwoven fabric layer m4 by means of the hot melt adhesive (not shown).

In the panel 3, the longitudinally opposite margins 19 and the transversely opposite lateral margins 20 of the nonwoven fabric layer m4 are joined to the respective inner surfaces of the second fibrous nonwoven fabric layer m2 and of the film m7 by means of the hot melt adhesive (not shown). The adhesive is intermittently applied on the nonwoven fabric layer m4 over its whole inner surface.

The end flaps 7 are defined by portions of the nonwoven fabric layers m1, m2, m4 extending outward beyond the longitudinally opposite ends 17 of the core m6. The side flaps 8 are defined by portions of the nonwoven fabric layers m1, m2, m4, m8 and the film m7 extending outward in the waist-circumferential direction beyond the transversely opposite side edges 18 of the core m6.

Figure 28:
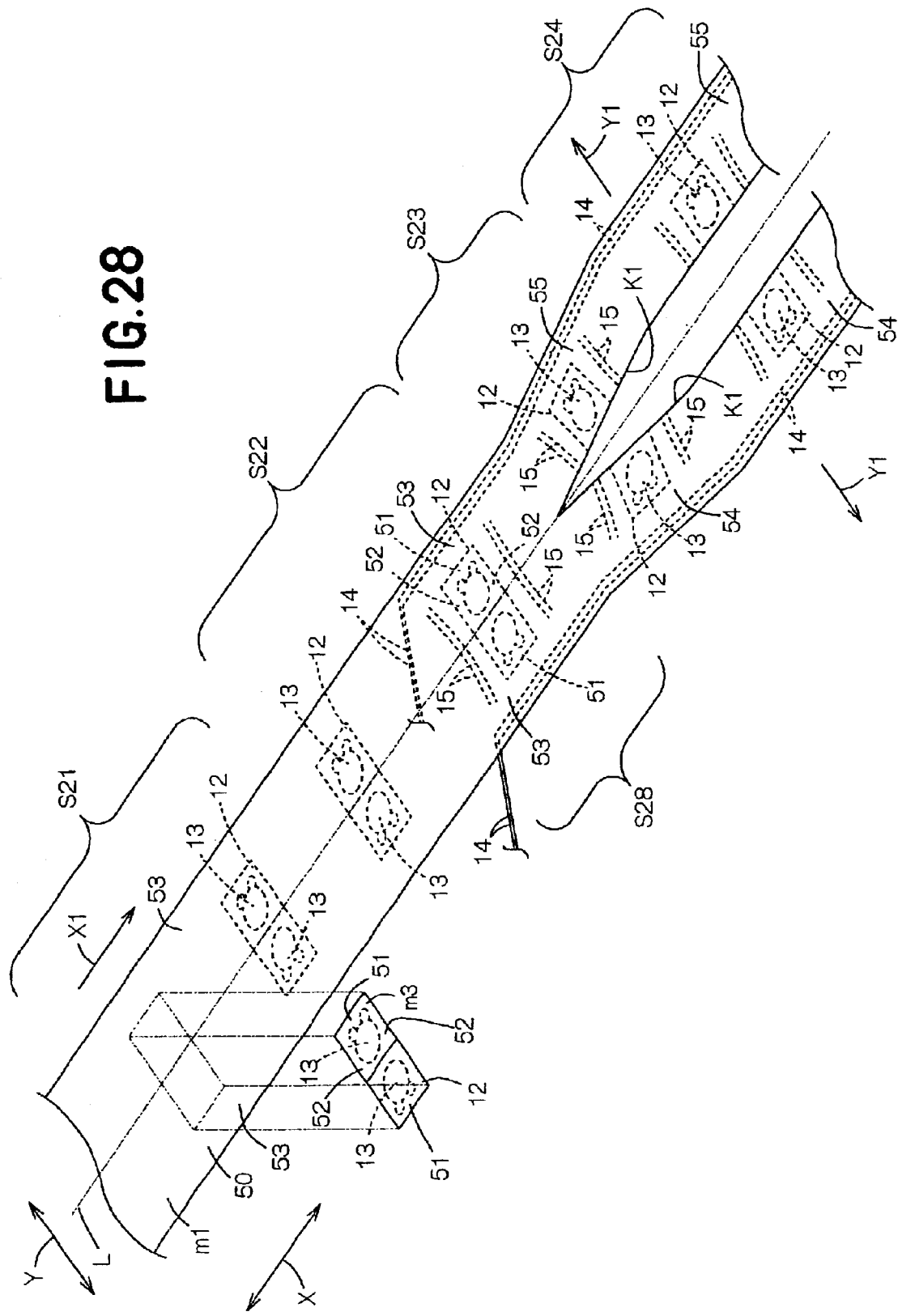
FIG. 28 is a perspective view schematically illustrating further alternative embodiment of the process for placing the indicator element.
Figure 29:
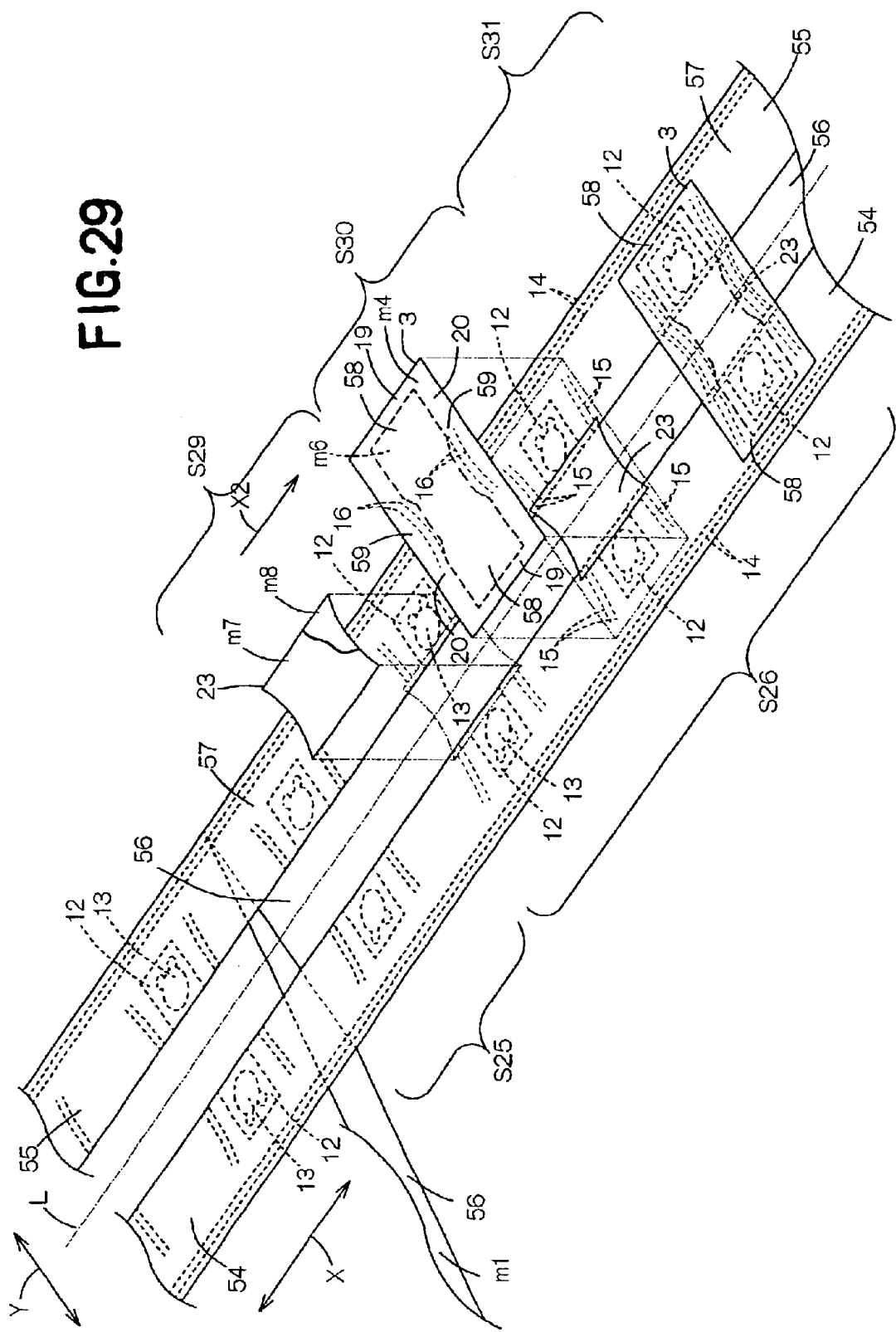
FIG. 29 is a perspective view schematically illustrating the steps subsequent to the steps in the process illustrated in FIG. 28.
Figure 30:
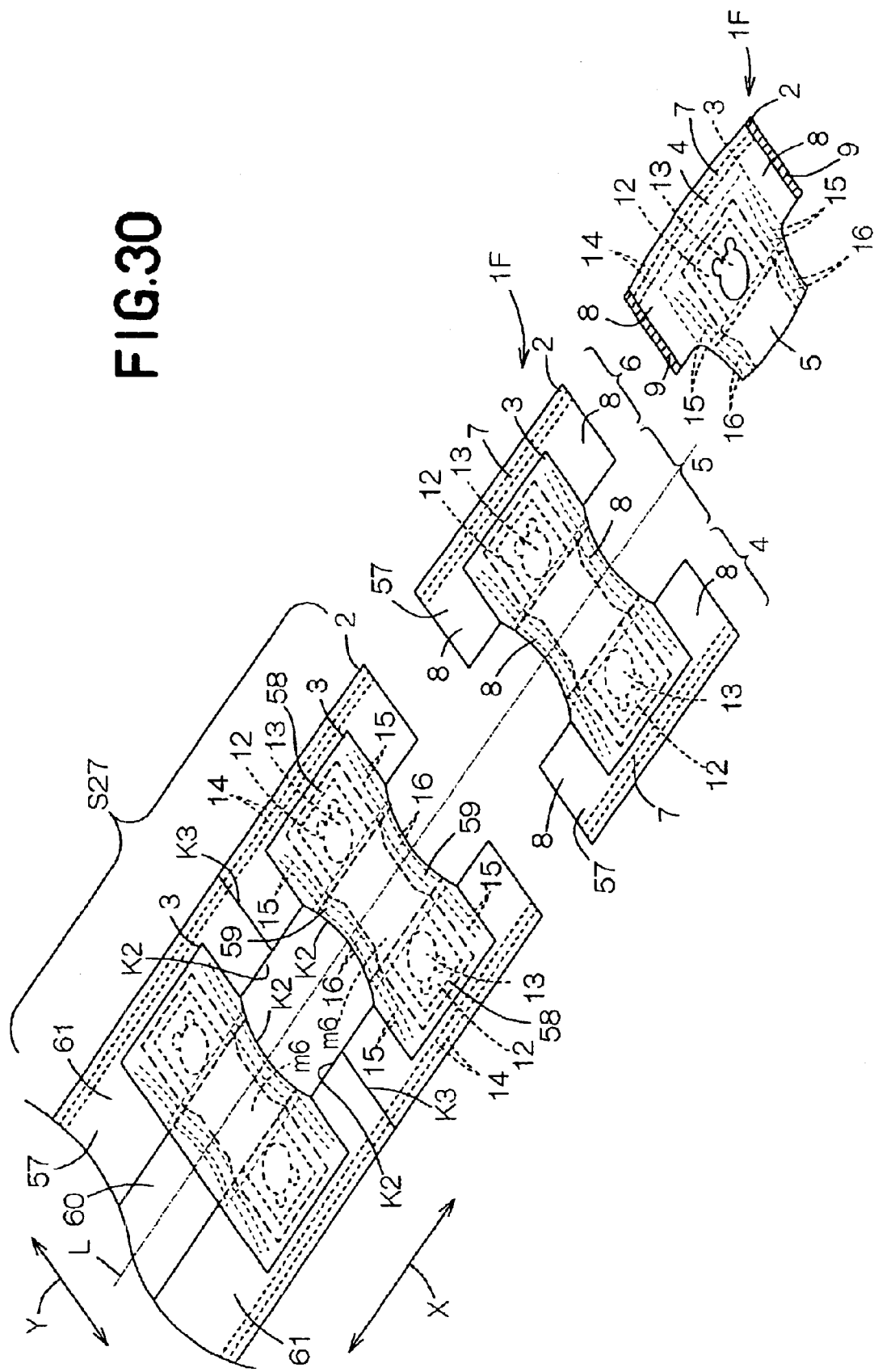
FIG. 30 is a perspective view schematically illustrating the steps subsequent to the steps in the process illustrated in FIG. 29.

FIG. 28 is a perspective view schematically illustrating further additional embodiment of the process for placing the indicator element, FIG. 29 is a perspective view schematically illustrating the steps subsequent to the steps in the process illustrated in FIG. 28 and FIG. 30 is a perspective view schematically illustrating the steps subsequent to the steps in the process illustrated in FIG. 29. Referring to these Figures, a machine direction (MD) is indicated by an arrow X and a cross direction (CD) is indicated by an arrow Y. According to this process, the article 1F of FIG. 26 is made and the indicator element is formed in the front and rear waist regions 4, 6 of the article 1F through successive steps as will be described.

Step S21: In the step S21, a plurality of the indication sheets 12 each having a pair of indicator elements 13 are successively fed under an inner web 50 continuously running in the MD.

The indication sheets 12 are placed under the inner web 50 so as to be spaced apart one from another by a predetermined dimension in the MD. The indicator elements 13 are a pair of illustrated bear's faces arranged side by side in mirror image relationship with each other.

The inner web 50 is formed by the breathable hydrophobic fibrous nonwoven fabric layer m2 (i.e., the second fibrous nonwoven fabric layer). The indication sheet 12 is formed by the breathable and liquid-impervious plastic film m3.

Step S22: In the step S22, the indication sheet 12 is joined to the under surface of the inner web 50 with the individual indicator elements 13 placed on both sides of the imaginary line L. The indication sheet 12 is joined to the inner web 50 by means of the hot melt adhesive (not shown) intermittently applied on the inner web 50 over its whole under surface.

In this step S22, a plurality of the first stretchable elastic members 14 (waist elastic members) continuously extending in the MD and a plurality of the second stretchable elastic members 15 (leg-circumferential direction) are secured in a stretched state to the under surface of the inner web 50. (step S28).

Step S23: In this step S23, the inner web 50, the indication sheet 12 and the elastic members 15 are cut along a cutting line K1 extending along the imaginary line L and bisected in the CD.

In the step S23, the inner web 50 is divided into first and second inner webs 54, 55 and at the same time each pair of the indicator elements 13 is divided into the individual indicator elements 13.

Step S24: In the step S24, the first and second inner webs 54, 55 are separated from each other by a predetermined dimension in the CD indicated by an arrow Y1 with pair of halves bisected from the indication sheet 12 being aligned with each other in the CD.

Step S25: In the step S25, an outer web 56 continuously running in the MD is placed under the first and second inner webs 54, 55 and then these first and second inner webs 54, 55 are joined to the outer web 56 by means of the hot melt adhesive with the indication sheets 12 interposed therebetween.

In this step S25, the first and second inner webs 54, 55 cooperate with the outer web 56 to form a composite web 57 (i.e., the composite nonwoven fabric layer 2). The indication sheet 12 and the outer web 56 are not joined. The outer web 56 is formed by the breathable hydrophobic fibrous nonwoven fabric layer m1 (i.e., the first fibrous nonwoven fabric layer).

Step S26: In the step S26, a plurality of the composite sheets 23 each extending in the CD are successively fed onto respective upper surfaces (inner surfaces) of the first and second inner webs 54, 55 and the outer web 56. Thus these composite sheets 23 are placed on the upper surfaces of these webs 54, 55, 56 so as to be spaced apart one from another in the MD by a predetermined dimension (step 29).

Each of the composite sheets 23 bridges the halves of the associated indication sheet 12 having been bisected and spaced apart from each other so as to overlay these halves of the indication sheet 12. Thus the composite sheets 23 are placed on the upper surface of the inner web 36 so as to be spaced apart one from another in the MD by a predetermined dimension. Then the under surface of the composite sheet 23 is joined to the respective upper surfaces of the first and second inner webs 54, 55 and the outer web 56 (step S30). The composite sheet 23 and these webs 54, 55, 56 are joined together by means of the hot melt adhesive (not shown) intermittently applied on nonwoven fabric layer m8 which will be described later over its whole under surface.

After the composite sheets 23 and those webs 54, 55, 56 have been joined together, a plurality of the liquid-absorbent laminated panels 3 are successively fed onto the upper respective surfaces of the composite sheets 23. The transversely opposite margins 58 of the panel 3 lie on the associated indication sheet 12. Then, the under surface of the panel 3 is joined to the upper surface of the associated composite sheet 23 by means of the hot melt adhesive (not shown) (step S31). At the same time, the transversely opposite margins 58 of the panel 3 are joined to the respective upper surfaces of the first and second inner webs 54, 55 by means of the hot melt adhesive (not shown).

Each of the composite sheets 23 presents an hourglass-like planar shape and comprises the breathable and liquid-impervious plastic film m7 and the breathable hydrophobic fibrous nonwoven fabric layer m8. The panel 3 comprises the breathable hydrophobic fibrous nonwoven fabric layer m4 and the liquid-absorbent core m6 underlying the nonwoven fabric layer m4 (See FIG. 27). The panel 3 is provided along its lateral margins 59 with the third stretchable elastic members 16 (leg elastic members) extending in the CD. These third stretchable elastic members 16 are secured in a stretched state to the panel 3.

In the panel 3, the under surface of the nonwoven fabric layer m4 is joined to the upper surface of the core m6 by means of the hot melt adhesive (not shown). The longitudinally opposite margins 19 and the transversely opposite lateral margins 20 of the nonwoven fabric layer m4 are joined to the upper surfaces of the inner webs 54, 55 as well as to the upper surface of the film m7 by means of the hot melt adhesive (not shown). The adhesive is intermittently applied on the nonwoven fabric layer m4 over its whole under surface.

The process may be implemented without departing the scope of the invention so that the composite sheets 23 are fed under the inner webs 54, 55 so as to be spaced apart one from another by a predetermined dimension in the MD in the step S25 and/or the upper surface of the composite sheet 23 is joined to the under surface of the inner webs 54, 55 in this step S5.

Step S27: In the step S27, the composite web 57 and the opposite lateral margins 59 of the panels 3 are cut along the lines K2, K3 extending across the composite web 57 between each pair of the adjacent panels 3.

In a transversely middle zone 60 of the composite web 57, each of the substantially square regions is cut out from assembly of the composite web 57 and the opposite lateral margins 59 of the panels 3 along the cutting line K2 of which a pair of transverse sections describe circular arcs being convex toward the core m6 and thereby cutouts destined to form a periphery of the leg-opening are obtained. At the same time, in the vicinity of the lateral zones 61 of the composite web 57, the composite web 57 is cut along the cutting line K3 rectilinearly extending in the CD. Those regions are cut out from the assembly of the composite web 57 and the opposite lateral margins 59 of the panels 3 in this manner to obtain a plurality of the individual articles 1F.

The article 1F obtained in this manner has a substantially hourglass-like planar shape to define, as viewed in the CD, the front waist region 4, the rear waist region 6 and the crotch region 5 extending between these waist regions 4, 6.

After the composite web 57 has been cut and the transversely opposite lateral margins 59 of the respective panels 3 have been trimmed, the composite web 57 and the associated panel 3 are folded along the imaginary line L with the panel 3 inside and the front waist region 4 and the rear waist region 6 both formed by the composite web 57 are placed upon each other. Then, these front and rear waist regions 4, 6 are joined together by means of the welding lines 9 to obtain the pull on-type article.

A stock material for the nonwoven fabric layers m1, m2, m4, m8 may be selected from the group consisting of products obtained by spun lace-, needle punch-, melt blown-, thermal bond-, spun bond-, chemical bond- and air through-processes. Component fibers for the nonwoven fabric layers may be selected from the group consisting of polyolefin-, polyester- and polyamide-based fibers and core-sheath type or side-by-side type conjugated fiber of polyethylene/polypropylene or polyethylene/polyester.

A stock material for the film layers m3, m5, m7 is preferably a polyolefin-based thermoplastic synthetic resin having a vapor-permeability in a range of 2150–4000 $g/m^2 \cdot 24$ hrs.

This invention is applicable not only to the pull on-type disposable wearing article 1A, 1B, 1C, 1D, 1E, 1F having its front and rear waist regions 4, 6 previously connected to each other but also to so-called an open-type disposable wearing article having its front and rear waist regions adapted to be connected to each other immediately before its actual use.

The process according to this invention for placing the indicator element has advantageous effects that the indication sheet having a pair of indicator elements is bisected and thereby the paired indicator elements are divided into the individual indicator elements so that the halves of the indication sheet thus bisected are spaced apart from each other by a given dimension and thereby the indicator elements can be placed on the surface of the article facing away from the wearer's body at once in the front and rear waist regions. This process makes it unnecessary to use means as well as steps for separately joining the individual indicator elements to the front and rear waist regions and correspondingly reduces the manufacturing cost of the article.

According to this process, each pair of the indicator elements printed on the indication sheet are in the mirror image relationship with each other and therefore there is no possibility that one of these indicator elements respectively placed on the front and rear waist regions might be placed upside down with respect to the other indicator element.

What is claimed is:

1. A process of placement of indicator elements in a disposable wearing article, which comprises a composite web and a liquid-absorbent panel joined to said composite web and includes front and rear waist regions and a crotch region between said waist regions, so that said indicator elements are visually recognizable from an exterior of said article, said process comprising the steps of:

placing indication sheets each having a pair of indicator elements arranged side by side in a cross direction onto a continuous outer web running in a machine direction so that said indication sheets are spaced apart one from another in said machine direction;

joining said indication sheets to said outer web with said indicator elements positioned on both sides of an imaginary line extending in said machine direction and bisecting said outer web along said imaginary line;

cutting said outer web and said indication sheets along said imaginary line to obtain a first outer web and a second outer web;

separating said first outer web and said second outer web from each other in said cross direction;

placing a continuous inner web running in said machine direction upon and joining said inner web to said first and second outer webs to obtain said composite web with said indication sheets being interposed between said outer web and said inner web;

feeding said liquid-absorbent panels onto said inner web of said composite web so that said panels are spaced apart one from another in said machine direction and joining said panels to said inner web of said composite web so as to overlay said indication sheets with said inner web being interposed between said panels and said indication sheets; and cutting said composite web between adjacent said panels.

2. The process according to claim 1, further comprising securing first stretchable elastic members in a stretched state to an upper surface of said outer web so as to extend continuously in said machine direction on both sides of said indication sheets; and securing second stretchable elastic members in a stretched state to said upper surface of said outer web so as to extend in said cross direction between adjacent said indication sheets.

3. The process according to claim 1, further comprising feeding composite sheets onto said inner web so that said composite sheets are spaced apart one from another and interposed between adjacent said indication sheets in said machine direction; and joining said inner web and said panels to said composite sheets.

4. The process according to claim 1, further comprising placing said inner web comprising first and second inner webs upon said first outer web and said second outer web, respectively;

joining said first inner web to said first outer web and said second inner web to said second outer web;

feeding composite sheets under said first and second outer webs so that said composite sheets are spaced apart one from another and interposed between adjacent said indication sheets in said machine direction; and joining said first and second outer webs and said panels to said composite sheets.

5. The process according to claim 1, further comprising placing said inner web comprising first and second inner webs upon said first outer web and said second outer web, respectively;

joining said first inner web to said first outer web and said second inner web to said second outer web;

feeding composite sheets onto said first and second outer webs so that said composite sheets are spaced apart one from another and interposed between adjacent said indication sheets in said machine direction; and joining said first and second outer webs and said panels to said composite sheets.

6. The process according to claim 3, wherein said outer web and said inner web are formed by a breathable hydrophobic fibrous nonwoven fabric, and each of said composite sheets is formed by a breathable liquid-impervious plastic film and a breathable hydrophobic fibrous nonwoven fabric placed upon each other.

7. The process according to claim 1, wherein each of said panels comprises a breathable hydrophobic fibrous nonwoven fabric and a liquid-absorbent core underlying said fibrous nonwoven fabric.

8. The process according to claim 1, wherein each of said indication sheets is formed by one of a breathable hydrophobic fibrous nonwoven fabric and a breathable liquid-impervious plastic film.

9. The process according to claim 1, wherein each of said indicator elements comprises an illustration printed on the respective indication sheet.

10. The process according to claim 1, wherein the indicator elements, which are printed on each of said indication sheets, are mirror images of each other.

11. A process of placement of indicator elements in a disposable wearing article, which comprises a composite web and a liquid-absorbent panel joined to said composite web and includes front and rear waist regions and a crotch region between said waist regions, so that said indicator elements are visually recognizable from an exterior of said article, said process comprising the steps of:

placing indication sheets each having a pair of indicator elements arranged side by side in a cross direction under a continuous inner web running in a machine direction so that said indication sheets are spaced apart one from another in said machine direction;

joining said indication sheets to said inner web with said indicator elements positioned on both sides of an imaginary line extending in said machine direction and bisecting said inner web along said imaginary line;

cutting said inner web and said indication sheets along said imaginary line to obtain a first inner web and a second inner web;

separating said first inner web and said second inner web from each other in said cross direction;

placing a continuous outer web running in said machine direction under and joining said outer web to said first and second inner webs to obtain said composite web with said indication sheets being interposed between said inner web and said outer web;

feeding said liquid-absorbent panels onto said first and second inner webs of said composite web so that said panels are spaced apart one from another in said machine direction and joining said panels to said first and second inner webs of said composite web so as to overlay said indication sheets with said first and second inner webs being interposed between said panels and said indication sheets; and cutting said composite web between adjacent said panels.

12. The process according to claim 11, further comprising securing first stretchable elastic members in a stretched state to an under surface of said inner web so as to extend continuously in said machine direction on both sides of said indication sheets; and securing second stretchable elastic members in a stretched state to said under surface of said inner web so as to extend in said cross direction between adjacent said indication sheets.

13. The process according to claim 11, further comprising feeding composite sheets onto said first and second inner webs so that said composite sheets are spaced apart one from another and interposed between adjacent said indication sheets in said machine direction; and joining said first and second inner webs and said panels to said composite sheets.

14. The process according to claim 13, wherein said outer web and said inner web are formed by a breathable hydrophobic fibrous nonwoven fabric, and each of said composite sheets is formed by a breathable liquid-impervious plastic film and a breathable hydrophobic fibrous nonwoven fabric placed upon each other.

15. The process according to claim 11, wherein each of said panels comprises a breathable hydrophobic fibrous nonwoven fabric and a liquid-absorbent core underlying said fibrous nonwoven fabric.

16. The process according to claim 11, wherein each of said indication sheets is formed by one of a breathable hydrophobic fibrous nonwoven fabric and a breathable liquid-impervious plastic film.

17. The process according to claim 11, wherein each of said indicator elements comprises an illustration printed on the respective indication sheet.

18. The process according to claim 11, wherein the indicator elements, which are printed on each of said indication sheets, are mirror images of each other.

* * * * *